(12) United States Patent
Dalecki et al.

(10) Patent No.: US 10,640,750 B2
(45) Date of Patent: May 5, 2020

(54) ULTRASOUND TECHNOLOGY TO CONTROL THE SPATIAL ORGANIZATION OF CELLS AND PROTEINS IN ENGINEERED TISSUES

(71) Applicant: University of Rochester, Rochester, NY (US)

(72) Inventors: Diane Dalecki, Rochester, NY (US); Denise Hocking, Rochester, NY (US); Kelley Garvin, San Jose, CA (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 0 days.

(21) Appl. No.: 15/606,828

(22) Filed: May 26, 2017

(65) Prior Publication Data
US 2017/0260504 A1    Sep. 14, 2017

Related U.S. Application Data

(62) Division of application No. 13/321,218, filed as application No. PCT/US2010/031281 on Apr. 15, 2010, now Pat. No. 9,688,962.
(Continued)

(51) Int. Cl.
| | | |
|---|---|---|
| *C12N 5/071* | (2010.01) | |
| *C12N 5/00* | (2006.01) | |
| *C12N 5/077* | (2010.01) | |
| *A61K 9/00* | (2006.01) | |
| *A61K 35/12* | (2015.01) | |

(Continued)

(52) U.S. Cl.
CPC .......... *C12N 5/069* (2013.01); *A61K 9/00* (2013.01); *A61K 35/12* (2013.01); *C12N 5/0062* (2013.01); *C12N 5/0656* (2013.01); *C12N 13/00* (2013.01); *C12Q 1/02* (2013.01); *C12Q 1/68* (2013.01); *C12N 2521/10* (2013.01); *C12N 2533/52* (2013.01); *C12N 2533/54* (2013.01)

(58) Field of Classification Search
None
See application file for complete search history.

(56) References Cited

U.S. PATENT DOCUMENTS

| | | | |
|---|---|---|---|
| 6,537,567 B1 | 3/2003 | Niklason et al. | |
| 2004/0175361 A1* | 9/2004 | Blaschuk ............ | A61K 9/0009 424/93.1 |

(Continued)

FOREIGN PATENT DOCUMENTS

| | | |
|---|---|---|
| EP | 1624922 B1 | 2/2006 |
| WO | 2002/092778 A2 | 11/2001 |

(Continued)

OTHER PUBLICATIONS

Wolburg et al., Cell Tissue Res. 335: 75-96 (2009).*
(Continued)

*Primary Examiner* — Erin M. Bowers
(74) *Attorney, Agent, or Firm* — Pepper Hamilton LLP

(57) ABSTRACT

The present invention is directed to methods of inducing spatial organization of cells an in vitro culture system using ultrasound technology. The invention is further directed to methods of inducing extracellular matrix remodeling and neovessel formation in an in vitro culture system and generating vascularized engineered tissue constructs using ultrasound technology.

15 Claims, 11 Drawing Sheets

Related U.S. Application Data

(60) Provisional application No. 61/179,646, filed on May 19, 2009.

(51) Int. Cl.
    *C12N 13/00* (2006.01)
    *C12Q 1/02* (2006.01)
    *C12Q 1/68* (2018.01)

(56) References Cited

U.S. PATENT DOCUMENTS

| | | | |
|---|---|---|---|
| 2005/0049640 | A1 | 3/2005 | Gurtner et al. |
| 2007/0299539 | A1 | 12/2007 | Othman et al. |
| 2008/0090292 | A1 | 4/2008 | Brooks et al. |
| 2009/0053686 | A1 | 2/2009 | Ward et al. |
| 2012/0058174 | A1 | 3/2012 | West et al. |

FOREIGN PATENT DOCUMENTS

| | | |
|---|---|---|
| WO | 2006/097707 A2 | 9/2006 |
| WO | 2008/119124 A1 | 10/2008 |

OTHER PUBLICATIONS

Shepherd, Proc. Nat'l. Acad. Sci. USA 100(22): 12535-12536 (2003).*
Ruoslahti, Glycobiology 6(5): 489-492 (1996).*
Dyson "Non-Thermal Cellular Effects of Ultrasound," British J. Cancer 45(Suppl V):165-171 (1982).
Gherardini et al. "A New Ultrasound-based Cell Immobilisation Technique," Proc. Forum Acusticum 2002 Sevilla, Spain, Special Session PHA-01: Acoustics of Dispersed Particulate Matter (2002).
International Search Report and Opinion for PCT/US2010/031281 dated May 27, 2010.
Hultstrom et al., "Proliferation and Viability of Adherent Cells Manipulated by Standing-Wave Ultrasound in a Microfluidic Chip," Ultrasound in Med. & Biol. 33(1):145-151 (2007).
Bazou et al., "Physical Environment of 2-D Animal Cell Aggregates Formed in a Short Pathlength Ultrasound Standing Wave Trap," Ultrasound in Med. & Biol. 31(3):423-430 (2005).
Hsu et al., "The Effect of Ultrasound Stimulation Versus Bioreactors on Neocartilage Formation in Tissue Engineering Scaffolds Seeded with Human Chondrocytes in Vitro," Biomol. Eng. 23(5):259-264 (2006).
Moinnes et al., "Ultrasound Accelerated Bone Tissue Engineering Monitored with Magnetic Resonance Microscopy," Conference Proceedings, Annual International Conference of the IEEE Engineering in Medicine and Biology Society, IEEE Cat. No. 06CH37748, pp. 484-488 (2006).
Garvin et al., "Controlling the Spatial Organization of Cells and Extracellular Matrix Proteins in Engineered Tissues Using Ultrasound Standing Wave Fields," Ultrasound Med. Biol.36(11):1919-1932 (2010).
Extended European Search Report for corresponding EP 10778079.3 (dated Feb. 1, 2013).
Schechner et al., "In vivo Formation of Complex Microvessels Lined by Human Endothelial Cells in an Immunodeficient Mouse," Proc Natl Acad Sci USA 97(16):9191-6 (2000).
Gherardini et al., "A New Immobilisation Method to Arrange Particles in a Gel Matrix by Ultrasound Standing Waves," Ultrasound Med Biol 31(2):261-72 (2005).
Garvin K., et al., "Ultrasound standing wave fields control the spatial distribution of cells and protein in three-dimensional engineered tissue", Journal of the Acoustical Society of America, vol. 125, No. 4, Apr. 8, 2009 (Apr. 8, 2009), pp. 2594-2594.
Examination Report for corresponding European Application No. 10 778 079.3 dated Sep. 17, 2013.
Rouwkema et al., "Endothelial Cells Assemble Into a 3-dimensional Prevascular Network in a Bone Tissue Engineering Construct," Tissue Eng 12(9):2685-93 (2006).
Raghavan et al., "Geometrically Controlled Endothelial Tubulogenesis in Micropatterned Gels," Tissue Engineering 16(7):2255-2263 (2010).
Ino et al., "Application of Magnetic Force-based Cell Patterning for Controlling Cell-cell Interactions in Angiogenesis," Biotechnol. Bioeng. 102(3):882-890 (2009).
Raz et al., "Cellular Alterations in Cultured Endothelial Cells Exposed to Therapeutic Ultrasound Irradiation," Endothelium 12(4):201-213 (2005).
Alberts et al., "Molecular Biology of the Cell," 4th Edition, New York: Garland Science, Chapter 22, Part 4: Blood Vessels and Endothelial Cells; http://ncbi.nim.nih.gov/books/NBK26848/, accessed Mar. 17, 2016.
Mizrahi et al., "Ultrasound-induced Angiogenic Response in Endothelial Cells," Ultrasound Med Biol 33(11):1818-29 (2007).

* cited by examiner

ULTRASOUND TECHNOLOGY TO CONTROL THE SPATIAL ORGANIZATION OF CELLS AND PROTEINS IN ENGINEERED TISSUES

This application is a divisional of U.S. patent application Ser. No. 13/321,218, filed Jan. 30, 2012, which is a national stage application under 35 U.S.C. § 371 of PCT Application No. PCT/US2010/031281, filed Apr. 15, 2010, which claims the benefit of 61/179,646, filed May 19, 2009, which are hereby incorporated by reference in their entirety.

This invention was made with government support under grant number R01EB008368 awarded by the National Institutes of Health. The government has certain rights in the invention.

FIELD OF THE INVENTION

The present invention is directed to methods of inducing cellular spatial organization, extracellular remodeling, and neovessel formation in an in vitro tissue culture system using ultrasound technology.

BACKGROUND OF THE INVENTION

Tissue and organ transplantation is a worldwide therapeutic approach for end-stage organ failure (Nasseri et al., "Tissue Engineering: An Evolving 21st-Century Science to Provide Biological Replacement for Reconstruction and Transplantation," *Surgery* 130:781-784 (2001)). Currently, over 100,000 people are in need of an organ transplant in the United States alone. Each day, 17-20 patients die while waiting for donor organs. These statistics highlight the worsening problem facing transplant patients—the demand for tissues and organs far outweighs the available supply. The field of tissue engineering offers great potential for reducing the number of patient deaths associated with this shortage of organs. By developing methods for repairing or replacing diseased or injured tissues and organs, tissue engineering aims to provide an alternative supply of tissues and organs to balance supply and demand (Langer et al., "Tissue Engineering," *Science* 260:920-926 (1993)). Before such a goal can be fully realized, tissue engineers need to successfully reconstitute viable tissues and organs in vitro, a task that depends on the delivery of essential nutrients and oxygen to all cells within the tissue to uphold their metabolic processes. Existing delivery methods include the passive diffusion of oxygen and nutrients through the tissue and host-dependent vascularization of the tissue after implantation (Nomi et al., "Principals of Neovascularization for Tissue Engineering," *Molecular Aspects of Medicine* 23:463-483 (2002); Lokmic et al., "Engineering the Microcirculation," *Tissue Engineering* 14(1):87-103 (2008); Tremblay et al., "Inosculation of Tissue-Engineered Capillaries with the Host's Vasculature in a Reconstructed Skin Transplanted on Mice," *American Journal of Transplantation* 5:1002-1010 (2005)). These methods are limited to tissues with less than a few millimeters in thickness and have therefore, only been successfully used for the development of skin replacements (Folkman et al., "Self-Regulation of Growth in Three Dimensions," *The Journal of Experimental Medicine* 138:745-753 (1973); Mooney et al., "Growing New Organs," *Scientific American* 280(4):60-65 (1999); Nomi et al., "Principals of Neovascularization for Tissue Engineering," *Molecular Aspects of Medicine* 23:463-483 (2002); Tremblay et al., "Inosculation of Tissue-Engineered Capillaries with the Host's Vasculature in a Reconstructed Skin Transplanted on Mice," *American Journal of Transplantation* 5:1002-1010 (2005); Griffith et al., "Diffusion Limits of an in Vitro Thick Prevascularized Tissue," *Tissue Engineering* 11(1-2):257-266 (2005)). As such, the engineering of larger, more complex, three-dimensional (3D) tissues and organs requires the in vitro development of a vascular system throughout the construct to adequately provide oxygen and nutrients to all areas of the tissue (Griffith et al., "Tissue Engineering-Current Challenges and Expanding Opportunities," *Science* 295:1009-1014 (2002); Nerem R. M., "Tissue Engineering: The Hope, the Hype, and the Future," *Tissue Engineering* 12:1143-1150 (2006); Jain et al., "Engineering Vascularized Tissue," *Nature Biotechnology* 23(7):821-823 (2005); Levenburg et al., "Engineering Vascularized Skeletal Muscle Tissue," *Nature Biotechnology* 23(7):879-884 (2005)).

Successful induction of neovessel network formation in tissue constructs depends on the stimulation of endothelial cell functions critical to angiogenesis. Endothelial cell survival, growth, migration and differentiation are influenced by the spatial distribution of endothelial cells and the organization of surrounding extracellular matrix ("ECM") (Korff et al., "Integration of Endothelial Cells in Multicellular Spheroids Prevents Apoptosis and Induces Differentiation," *The Journal of Cell Biology* 143(5):1341-1352 (1998); Ino et al., "Application of Magnetic Force-Based Cell Patterning for Controlling Cell-Cell Interactions in Angiogenesis," *Biotechnology and Bioengineering* 102(3):882-890 (2009); Vailhe et al., "In Vitro Models of Vasculogenesis and Angiogenesis," *Laboratory Investigation* 81(4):439-452 (2001); Nehls et al., "The Configuration of Fibrin Clots Determines Capillary Morphogenesis and Endothelial Cell Migration," *Microvascular Research* 51:347-364 (1996); Vailhe et al., "In Vitro Angiogenesis is Modulated by the Mechanical Properties of Fibrin Gels and is Related to Alpha-v Beta-3 Integrin Localization," In *Vitro Cell. Dev. Biol.-Animal* 33:763-773 (1997); Ingber et al., "Mechanochemical Switching between Growth and Differentiation During Fibroblast Growth Factor-Stimulated Angiogenesis In Vitro: Role of Extracellular Matrix," *The Journal of Cell Biology* 109:317-330 (1989); Stephanou et al., "The Rigidity in fibrin Gels as a Contributing Factor to the Dynamics of In Vitro Vascular Cord Formation," *Microvascular Research* 73:182-190 (2007); Sieminski et al., "The Relative Magnitudes of Endothelial Force Generation and Matrix Stiffness Modulate Capillary Morphogenesis In Vitro," *Experimental Cell Research* 297:574-584 (2004; and Montesano et al., "In Vitro Rapid Organization of Endothelial Cells into Capillary-Like Networks is Promoted by Collagen Matrices," *The Journal of Cell Biology* 97:1648-1652 (1983), which are hereby incorporated by reference in their entirety). As such, control over both endothelial cell and ECM protein organization within 3D tissue constructs will affect endothelial cell functions essential to angiogenesis.

Technologies currently in development to organize cells and proteins into complex patterns can be divided into two general categories. In the first approach, micropatterning of cell-adhesive contacts using extracellular matrix proteins coated onto microfabricated stamps by photolithography or microcontact printing is used to direct cell adhesion into pre-designed patterns. In the second approach, a force is applied to cells to direct cell movement to a desired location. The applied force can be optical, magnetic, electrokinetic, or fluidic ((Lin et al., "Dielectrophoresis Based-Cell Patterning for Tissue Engineering," *Biotechnol J* 1:949-57 (2006)). The ability of acoustic radiation forces associated with ultrasound standing wave fields to control the spatial distribution of cells and extracellular matrix proteins in a three-dimensional tissue model has not previously been investigated.

When an ultrasonic pressure wave is incident on an acoustic reflector, the reflected wave interferes with the incident wave resulting in the development of an ultrasound standing wave field (USWF). An USWF is characterized by areas of maximum pressure, known as pressure antinodes, and areas of zero pressure, known as pressure nodes. Exposure of particle or cell suspensions to an USWF can result in the alignment of particles or cells into bands that are perpendicular to the direction of sound propagation and that are spaced at half-wavelength intervals (Coakley et al., "Cell Manipulation in Ultrasonic Standing Wave Fields," *J Chem Tech Biotechnol* 44:43-62 (1989); Gould et al., "The Effects of Acoustic Forces on Small Particles in Suspension," *In: Finite amplitude wave effects in fluids: Proceedings of the 1973 Symposium*, Guildford: IPC Science and Technology Press Ltd, Bjorno L, ed. pp. 252-7 (1974); and Whitworth et al., "Particle Column Formation in a Stationary Ultrasonic Field," *J Acoust Soc Am* 91:79-85 (1992)). A primary acoustic radiation force, ($F_{rad}$), generated along the direction of sound propagation in the USWF, is largely responsible for this movement. $F_{rad}$ is defined as $$F_{rad} = \left(\frac{-\pi P_o^2 V \beta_o}{2\lambda}\right) * \phi * \sin\left(\frac{4\pi z}{\lambda}\right) \quad \text{(Equation 1)}$$

where $P_o$ is the USWF peak pressure amplitude, V is the spherical particle volume, $\lambda$ is the wavelength of the sound field, z is the perpendicular distance on axis from pressure nodal planes, and $\varphi$ is an acoustic contrast factor given by $$\phi = \frac{5\rho_p - 2\rho_o}{2\rho_p + \rho_o} - \frac{\beta_p}{\beta_o} \quad \text{(Equation 2)}$$

where $\rho_p$ and $\beta_p$ are the density and compressibility of the particles or cells, and $\rho_o$ and $\beta_o$ are the density and compressibility of the suspending medium, respectively (Gol'dberg Z A, "Radiation Forces Acting on a Particle in a Sound Field," *In: High Intensity Ultrasonic Fields*, New York: Plenum Press, Rozenberg L D, ed., pp. 109-17 (1971); Gor'kov L P, "On the Forces Acting on a Small Particle in an Acoustical Field in an Ideal Fluid," *Sov Phys Dokl* 6:773-5 (1962); and Gould et al., "The Effects of Acoustic Forces on Small Particles in Suspension," *In: Finite amplitude wave effects in fluids: Proceedings of the 1973 Symposium*, Guildford: IPC Science and Technology Press Ltd, Bjorno L, ed. pp. 252-7 (1974). The forces generating the banded pattern exist only during application of the USWF. Therefore, to maintain the USWF-induced banded distribution, suspending mediums have been used that undergo a phase conversion from a liquid to a solid state during USWF exposure (Gherardini et al., "A Study of the Spatial Organisation of Microbial Cells in a Gel Matrix Subjected to Treatment With Ultrasound Standing Waves," *Bioseparation* 10:153-62 (2002); Gherardini et al., "A New Immobilisation Method to Arrange Particles in a Gel Matrix by Ultrasound Standing Waves," *Ultrasound Med Biol* 31:261-72 (2005); Saito et al., "Fabrication of a Polymer Composite With Periodic Structure by the Use of Ultrasonic Waves," *J Appl Phys* 83:3490-4 (1998); and Saito et al.," "Composite Materials With Ultrasonically Induced Layer or Lattice Structure," *Jpn J Appl Phys* 38:3028-31 (1999)). In this way, the banded pattern is retained after removal of the sound field.

The present invention is directed to overcoming these and other deficiencies in the art.

SUMMARY OF THE INVENTION

A first aspect of the present invention is directed to a method of inducing spatial organization of cells in an in vitro culture system. This method involves providing an in vitro culture system having cells and a biological support material and placing the in vitro culture system in an ultrasound exposure chamber. The method further involves exposing the in vitro culture system to an ultrasound standing wave field under conditions effective to induce cellular spatial organization and incubating the in vitro culture system containing the spatially organized cells under conditions effective to permit cell behavior important for tissue generation.

A second aspect of the present invention is directed to a method of inducing neovessel formation in an in vitro culture system. This method involves providing an in vitro culture system comprising a biological support material and endothelial cells, and placing the in vitro culture system in an ultrasound exposure chamber. The method further involves exposing the in vitro culture system to an ultrasound standing wave field under conditions effective to spatially organize endothelial cells, and incubating the in vitro culture system containing the spatially organized endothelial cells under conditions effective to induce neovessel formation.

Another aspect of the present invention is directed to a vascularized engineered tissue construct. This vascularized engineered tissue construct has a three-dimensional thickness of at least 2 mm.

Methods of promoting angiogenesis throughout three dimensional engineered tissue are needed to fabricate large vascularized tissues and organs for the field of tissue engineering. Angiogenic cell behaviors are modulated by the spatial arrangement of endothelial cells, the organization of their surrounding extracellular matrix (ECM), and by mechanical force application. The present invention demonstrates that ultrasound technology is capable of controlling all three of these regulatory factors and can induce spatial organization of both cells and proteins and subsequently vascularization within three dimensional engineered tissue constructs. The present invention will allow for the successful reconstitution of viable tissues and organs in vitro, making it possible to repair or replace diseased or injured tissues and organs.

BRIEF DESCRIPTION OF THE DRAWINGS

FIG. 1A shows the ultrasound wave field exposure system. A thick rubber absorber is placed above a sealed, submerged sample holder for ultrasound traveling wave field (UTWF) exposures. FIG. 1B is an enlarged view of the silicone elastomer-bottomed (acoustic attenuation of 0.06 dB) sample holder (FlexCell Inc., Hillsborough, N.C.). Well diameters were decreased to 1 cm using Sylgard 184® Silicone Elastomer (Dow Corning, Midland, Mich.) molds to fit the sample size to the dimensions of the ultrasound beam.

In FIG. 8A, fibronectin-null cells ($4\times10^6$ cell/ml) suspended in collagen I solutions were exposed at room temperature for 15 min to a continuous wave USWF (1 MHz source) with various peak pressure amplitudes. Following 1 hr incubation at 37° C. and 8% $CO_2$, gel diameters were measured. Data are presented as average percent radial gel contraction±SEM and are normalized to the sham condition (n=10). The * indicates a difference from sham group (p<0.05). In FIG. 8B, fibronectin-null cells ($2\times10^5$ cell/ml) suspended in a collagen I solutions were exposed at room temperature for 15 min to a continuous wave USWF (1 MHz source) with peak pressure amplitude of 0.3 MPa. Following 1 hr incubation at 37° C. and 8% $CO_2$, cell viability was assessed using MTT. Data are presented as average fold difference in absorbance±SEM normalized to sham average absorbance values (n=3; p>0.05).

DETAILED DESCRIPTION OF THE INVENTION

Figure 1A:
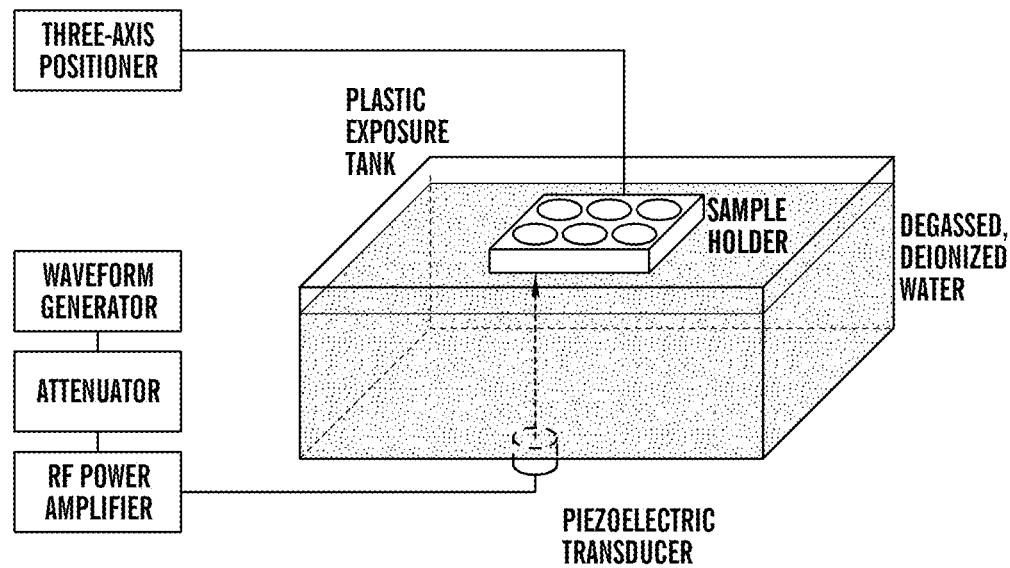
FIGS. 1A-1B are schematic representations of the experimental set-up for exposing in vitro cell culture systems to ultrasound standing wave field (UWSF).

A first aspect of the present invention is directed to a method of inducing spatial organization of cells in an in vitro culture system. This method involves providing an in vitro culture system having cells and a biological support material and placing the in vitro culture system in an ultrasound exposure chamber. The method further involves exposing the in vitro culture system to an ultrasound standing wave field under conditions effective to induce cellular spatial organization, and incubating the in vitro culture system containing the spatially organized cells under conditions effective to permit cell behavior important for tissue generation.

As used herein, an in vitro culture system refers to any two or three dimensional culture of living cells or tissue, preferably mammalian cells or tissue, produced primarily by growth in vitro. The in vitro culture system of the present invention may include one or more types of cells or tissues. The cells of the in vitro system may be primary cell cultures, cell lines, or a combination of both. Suitable cell types include, but are not limited to, smooth muscle cells, cardiac muscle cells, cardiac myocytes, platelets, epithelial cells, endothelial cells, endothelial progenitor cells, urothelial cells, fibroblasts, embryonic fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, adipocytes, embryonic stem cells, mesenchymal stem cells, hematopoietic cells, neural cells, and precursor cells.

In accordance with this aspect of the present invention, the in vitro culture system containing spatially organized cells is incubated under conditions effective to permit cell behavior important for tissue generation. Tissue generation as used herein refers to both de novo tissue generation and tissue regeneration. Cell behaviors that are involved in tissue generation include, without limitation, cell survival, cell growth, cell differentiation, cell migration, changes in gene expression, and extracellular matrix remodeling. Tissue generation can be measure or assessed by any one or more of the above identified cell behaviors.

In one embodiment of the present invention, the in vitro tissue culture system is one having a configuration that is amenable to the generation of an engineered tissue construct. An engineered tissue construct is a three dimensional mass of living mammalian tissue produced primarily by growth in vitro that shares critical structural and functional characteristics with intact tissue, such as distinctive multicellular organization and oriented contractile function. Engineered tissue constructs generated using the methods of the present invention can be any desired tissue construct including, but not limited to, a muscular construct, a vascular construct, an esophageal construct, an intestinal construct, a rectal construct, an ureteral construct, a cartilaginous construct, a cardiac construct, a liver construct, a bladder construct, a kidney construct, a pancreatic construct, a skeletal construct, a filamentous/ligament construct, a lung construct, a neural construct, a bone construct, and a skin construct.

In accordance with this aspect of the present invention, the biological support material of the in vitro culture system consists of a biological material that supports the growth and survival of living cells and tissue under in vitro conditions. In an embodiment of the present invention, the biological support material of the in vitro culture system is a polymerizable culture media. Suitable polymerizable culture media solutions include, without limitation, collagen, collagen type-I, alginate, growth factor reduced Matrigel, Matrigel, hydrogel, and fibrin, any of which may be supplemented with suitable proteinaceous materials (e.g., chitosan, hyaluronan, polyethylene oxide/polypropylene oxide). The gel may further include one or more of laminin, fibrin, fibronectin, proteoglycans, glycoproteins, glycosaminoglycans, chemotactic agents, or growth factors, for example, cytokines, eicosanoids, or differentiation factors. Upon polymerization of the culture media solution, a three-dimensional culture environment is formed.

In another embodiment of the present invention, the in vitro culture system includes a biological support material that promotes three dimensional cellular and tissue growth and expansion. In general, these supports are three-dimensional and are processable to form scaffolds of a desired shape for the tissue of interest. Suitable three dimensional biological supports include, without limitation, filaments, meshes, foams, gels, ceramics, and acellularized extracellular matrix material. The biological support substrate preferably consists of a biocompatible material, e.g., a biocompatible polymer having properties or incorporating modifications conducive to cell adherence and/or growth. In one embodiment, the support material is a porous polymer as described in U.S. Pat. No. 6,103,255 to Levene, which is hereby incorporated by reference in its entirety. In another embodiment, the support material is biodegradable or bioerodable, including those materials that hydrolyze slowly under physiological conditions. Suitable materials, include synthetic polymeric materials such as polyesters, polyorthoesters, polylactic acid, polyglycolic acid, polycaprolactone, or polyanhydrides, including polymers or copolymers of glycolic acid, lactic acid, or sebacic acid. Substrates comprising proteinaceous polymers are also suitable for use in the methods of the present invention. Collagen gels, collagen sponges and meshes, and substrates based on elastin, fibronectin, laminin, or other extracellular matrix or fibrillar proteins may also be employed. Either synthetic polymers or proteinaceous polymers may be modified or derivatized in any of a variety of ways, e.g., to increase their hydrophilicity and/or provide improved cell adhesion characteristics. In certain embodiments of the present invention, the substrate may be coated with an agent, e.g., denatured collagen, prior to seeding in order to increase cellular adherence. Materials useful as substrates for growing cells to produce tissue engineered substrates, and methods of producing such substrates are known in the art and are described in U.S. Pat. No. 5,770,417 to Vacanti et al., which is hereby incorporated by reference in its entirety.

Other suitable biological support materials that can be used in the methods of the present invention include the multilayer scaffold described in U.S. Pat. No. 6,143,292 to Weiss et al., which is hereby incorporated by reference in its entirety; the three dimensional geometric biocompatible porous scaffold described in U.S. Pat. No. 6,206,924 to Timm, which is hereby incorporated by reference in its entirety; the three dimensional matrix containing fibrin matrix described in U.S. Patent Application Publication No. 20030166274; and the hyaluronan based biodegradable scaffold described in U.S. Pat. No. 5,939,323, which is hereby incorporated by reference in its entirety.

The in vitro culture system is cultured or maintained using standard tissue culture procedures. Appropriate growth and culture conditions for various mammalian cell types are well known in the art. The cells in the in vitro cell culture system may be seeded onto and/or within a substrate from a suspension so that they are evenly distributed at a relatively high surface and/or volume density. The cell suspensions may comprise approximately about $1\times10^4$ to about $5\times10^7$ cells/ml of culture medium, or approximately about $2\times10^6$ cells/ml to about $2\times10^7$ cells/ml, or approximately about $5\times10^6$ cells/ml. The optimal concentration and absolute number of cells will vary with cell type, growth rate of the cells, substrate material, and a variety of other parameters. The suspension may be formed in any physiologically acceptable medium, preferably one that does not damage the cells or impair their ability to adhere to the substrate. Appropriate mediums include standard cell growth media (e.g., DMEM with 10% FBS).

Examples of suitable seeding and culturing methods for the growth of three-dimensional cell cultures, including techniques for establishing a three-dimensional matrix, inoculating the matrix with the desired cells, and maintaining the culture are disclosed in U.S. Pat. No. 6,537,567 to Niklason et al., U.S. Pat. No. 5,266,480 to Naughton et al., and U.S. Pat. No. 5,770,417 to Vacanti et al., which are hereby incorporated by reference in their entirety. Alternatively, the cells of the in vitro system can be suspended in a polymerizable cell media and seeded into an appropriate culture dish or onto an appropriate substrate as described herein. Suitable substrates can be flat, tubular, or configured to assume any desired three-dimensional shape (e.g., spheres, ellipsoids, disks, sheets, or films as well as hollow spheres, hollow ellipsoids, and open-ended, hollow tubes).

Cells of the in vitro culture system are cultured in a media that generally includes essential nutrients and, optionally, additional elements such as growth factors, salts, minerals, vitamins, etc., that may be selected according to the cell type(s) being cultured. A standard growth media includes Dulbecco's Modified Eagle Medium, low glucose (DMEM), with 110 mg/L pyruvate and glutamine, supplemented with 10-20% fetal bovine serum (FBS) or calf serum and 100 U/ml penicillin. The culture media may also contain particular growth factors selected to enhance cell survival, differentiation, secretion of specific proteins, etc. In accordance with this aspect of the present invention, factors that enhance cell growth, proliferation, and differentiation may be added to the in vitro culture system.

In accordance with this aspect of the present invention the in vitro culture system may further contain one or more particles that are also responsive to the ultrasound wave field exposure as described herein. These particles include, without limitation, nanoparticles, microparticles, microbubbles, and cells. In a preferred embodiment of the present invention, these particles contain or have bound thereto biologically active peptides, proteins, or peptide or protein mimetics. Suitable peptides, proteins, and protein mimetics include for example growth factors (e.g., VEGF or FGF), adhesion proteins, extracellular matrix proteins (e.g., fibronectin, recombinant fibronectin fragments, or vitronectin), angiogenic factors, etc. In a preferred embodiment of the present invention, the biologically active peptide, protein, or protein mimetic is a biologically active fibronectin peptide, protein, or protein mimetic.

Once the desired in vitro culture system has been established, the culture system is exposed to an ultrasound wave field under conditions effective for inducing cellular spatial organization. This spatial organization of cells within the in vitro culture system facilitates key cellular functions, such as survival, growth, migration, and differentiation. In addition, as demonstrated herein, the spatial organization of cells in the in vitro culture system facilitates extracellular matrix remodeling thereby enhancing the mechanical strength of the cultured cells and tissue.

Ultrasound ("US") is a form of mechanical energy that travels through a medium of propagation as an acoustic pressure wave at frequencies above 20 kHz. It is used widely in the medical field as both a diagnostic and therapeutic tool (Duck et al., "Ultrasound In Medicine," Philadelphia: Institute of Physics Publishing (1998), which is hereby incorporated by reference in its entirety). US can interact with biological tissues through thermal or mechanical mechanisms (Dalecki D., "Mechanical Bioeffects of Ultrasound," *Annu. Rev. Biomed. Eng.* 6:229-248 (2004), which is hereby incorporated by reference in its entirety). Mechanical interactions, associated with the generation of US-induced mechanical forces in the medium of propagation, can produce US bioeffects (Dalecki D., "Mechanical Bioeffects of Ultrasound," *Annu. Rev. Biomed. Eng.* 6:229-248 (2004), which is hereby incorporated by reference in its entirety). For example, red blood cells redistribute to equally spaced intervals due to USWF radiation forces (Dyson et al., "The Production of Blood Cell Stasis and Endothelial Damage in the Blood Vessels of Chick Embryos Treated with Ultrasound in a Stationary Wave Field," *Ultrasound in Medicine and Biology* 1:133-148 (1974), which is hereby incorporated by reference in its entirety). Also, low-intensity pulsed US enhances nitric oxide production in endothelial cells, a well-documented endothelial cell response to shear stress and stimulates fibroblast growth through a signaling pathway known to be triggered by direct mechanical stimulation (Altland et al., "Low-Intensity Ultrasound Increases Endothelial Cell Nitric Oxide Synthase Activity and Nitric Oxide Synthesis," *Journal of Thrombosis and Haemostasis* 2:637-643 (2004) and Zhou et al., "Molecular Mechanisms of Low Intensity Pulsed Ultrasound in Human Skin Fibroblasts," *The Journal of Biological Chemistry* 279(52): 54463-54469 (2004), which are hereby incorporated by reference in their entirety).

In accordance with the methods of the present invention, ultrasound exposure mediated "spatial organization" of cells in the in vitro cell culture system encompasses the alignment of cells into parallel sheets, planes, columns, and/or grid matrices. As demonstrated herein, exposure of the in vitro culture system of the present invention to an ultrasound standing wave field results in the alignment of cells in the system into bands that are perpendicular to the direction of sound propagation and that are spaced at half-wavelength intervals. As discussed supra, the in vitro cultures system of the present invention may also include one or more particles that are also responsive to ultrasound exposure mediated spatial organization. In one embodiment of the present invention, exposure of the particles (e.g. proteins bound to cells) to an ultrasound wave field will localize the particles to the pressure node, thereby co-localizing the particles with the cells of the in vitro culture system. Co-localization of the particles and cells will provide cells of the system the necessary and specific signals and growth factors that mediate cell growth, proliferation, or differentiation in a controlled manner. In another embodiment of the present invention, exposure of the particles (e.g. microbubbles) to an ultrasound wave field will localize the particles to the pressure anti-nodes resulting in a staggered arrangement of the particles and cells of the in vitro culture system. This staggered arrangement of particles and cells will generate a concentration gradient of growth factors or matrix proteins contained in the particles between the spatially organized cells. The concentration gradients will enhance phenotypic differentiation of the spatially organized cells (e.g., enhance neovessel formation of endothelial cell bands).

Prior to ultrasound wave field exposure, the in vitro culture system is placed in a suitable ultrasound exposure chamber, such as the one described herein. This exposure chamber consists of a degassed chamber of deionized water in a plastic exposure tank. The in vitro culture system is sealed and submerged into the exposure tank via a sample holder. The sample holder aligns the in vitro culture system with the ultrasound wave beam to facilitate direct exposure. The exposure chamber can further include a means for controlling the sample/air interface (e.g., a rubber absorber) to allow for ultrasound standing or traveling wave fields to be generated in the same exposure chamber.

The parameters of ultrasound wave field exposure of the in vitro culture system will vary depending on the cell type, biological support material, and desired endpoint (e.g. spatial organization), and should be optimized for each in vitro culture system to produce optimal results. These parameters include, for example, acoustic pressure amplitude, frequency, and exposure duration. Methods for optimizing these ultrasound exposure parameters are described herein.

In accordance with this aspect of the present invention, the in vitro culture system is exposed to an ultrasound standing wave field. The cells and particles of the in vitro culture system may be exposed to one or more ultrasound standing wave beams at one time depending on the desired spatial organization. Exposure to one beam of ultrasound is sufficient for spatially organizing cells in planes and columns. Alternatively, multiple intersecting beams of ultrasound can be used to spatially arrange cells and/or particles into a grid matrix and columns. Various transducer geometries and set-ups can be utilized to achieve the desired spatial arrangement or organization of cells in the system. The ultrasound standing wave field exposure may involve exposure of the in vitro culture system to a continuous wave signal or a pulsating wave signal. If a pulsating wave signal exposure is employed the appropriate pulse frequency and duration must be optimized.

In accordance with this aspect of the present invention, exposure to the ultrasound standing wave field is carried out at a pressure amplitude that is optimal for mediating the spatial organization of cells in the in vitro culture system. In one embodiment, cells of the in vitro culture system are exposed to ultrasound pressure amplitude of about 0.01 MPa to about 0.5 MPa. Likewise, the ultrasound frequency should be also be optimized to ensure a frequency that promotes spatial organization and neovessel formation is employed. In one embodiment, the exposure of the in vitro culture system to an ultrasound energy source is at a frequency of from about 0.02 MHz to about 20 MHz. More preferably the exposure to an ultrasound energy source is at a frequency of from about 0.1 MHz to about 3 MHz. Most preferably, the ultrasound is applied at a frequency of about 1 MHz.

The duration of ultrasound exposure will vary depending on the tissue type of the in vitro culture system. In one embodiment, ultrasound exposure is carried out for a period of about 10 seconds to about 60 minutes. In another embodiment the exposure is for a period of about 60 seconds to about 20 minutes. In another embodiment, the ultrasound is applied for about 15 minutes. Exposure of the in vitro culture system to the ultrasound standing wave may be repeated one or more times a day, a week, or a month.

In another embodiment of the present invention, the spatially organized cells of the in vitro culture system are further exposed to an ultrasound traveling wave field. Exposure to an ultrasound traveling wave field will facilitate cell growth, survival, proliferation, and phenotypic differentiation of the spatially organized cells of the in vitro culture system. Exposure of the spatially organized cells of the in vitro system can be carried out for any suitable duration of time. Preferably, the duration of exposure is between about 10 seconds and about 60 minutes. In another embodiment, the exposure is for a period of about 60 seconds to 20 minutes. In yet another embodiment, the exposure is carried out for a period of about 10 minutes. Exposure of the in vitro culture system to the ultrasound traveling wave may be repeated one or more times a day, a week, or a month.

The parameters of ultrasound traveling wave exposure must be optimized in accordance with the particular in vitro culture system utilized based on cell type, biological support material, and particle type. In one embodiment, the exposure of the in vitro culture system to an ultrasound energy source is at a frequency of about 0.02 MHz to about 20 MHz. In another embodiment, the exposure to an ultrasound energy source is at a frequency of about 0.1 MHz to about 3 MHz. Alternatively, the ultrasound is applied at a frequency of about 1 MHz.

Exposure of the in vitro culture system may consist of a continuous traveling wave exposure or a pulsating traveling wave exposure. When a pulsed ultrasound exposure is employed, the pulse frequency and duration must also be optimized. In a preferred embodiment, the in vitro culture system is exposed to an ultrasonic field pulsed at 1 kHz with a 200 μs pulse duration.

Therapeutic ultrasound treatments that enhance wound healing have been hypothesized to do so by promoting the growth of blood vessels within the wound space (Young et al., "The Effect of Therapeutic Ultrasound on Angiogenesis," *Ultrasound in Medicine and Biology* 16:261-269 (1990), which is hereby incorporated by reference in its entirety). In fact, similar ultrasound exposure protocols have been shown to enhance both tissue healing and angiogenesis (Young et al., "The Effect of Therapeutic Ultrasound on Angiogenesis," *Ultrasound in Medicine and Biology* 16:261-269 (1990) and Dyson et al., "The Stimulation of Tissue Regeneration by Means of Ultrasound," *Clinical Science* 35:273-285 (1968), which are hereby incorporated by reference in their entirety). Exposure to the aforementioned growth-promoting UTWF is expected to enhance neovessel formation in 3D collagen gels. Therefore, it may be desirable to expose USWF-induced spatially organized cells to the UTWF exposure regimen as described supra. As therapeutic ultrasound exposure enhances both the number of blood vessels in the wound space (Barzelai et al., "Low-Intensity Ultrasound Induces Angiogenesis in Rat Hind-Limb Ischemia," *Ultrasound in Medicine and Biology* 32(1): 39-145 (2006) and Young et al., "The Effect of Therapeutic Ultrasound on Angiogenesis," *Ultrasound in Medicine and Biology* 16:261-269 (1990), which are hereby incorporated by reference in their entirety) and the length of newly formed capillary structures (Mizrahi et al., "Ultrasound-Induced Angiogenic Response in Endothelial Cells," *Ultrasound in Medicine and Biology* 33(11):1818-1829 (2007), which is hereby incorporated by reference in its entirety), it is expected that USWF-induced cell and protein organization and UTWF exposure will combine to promote angiogenesis for the vascularization of 3D tissue constructs.

Following ultrasound wave field exposure of the in vitro culture system of the present invention, the culture system is maintained under conditions effective to facilitate cell or tissue survival, growth, proliferation, differentiation, gene expression, migration, and extracellular matrix remodeling. Suitable conditions will depend on the cells or tissue of the in vitro culture system.

A second aspect of the present invention is directed to a method of inducing extracellular matrix remodeling in an in vitro culture system. This method involves providing an in vitro culture system having a biological support material and placing the in vitro culture system in an ultrasound exposure chamber. The method further involves exposing the in vitro culture system to an ultrasound standing wave field under conditions effective to induce extracellular matrix remodeling, and incubating the in vitro culture system under conditions to permit extracellular matrix remodeling.

As demonstrated in the Examples described herein, ultrasound exposure is capable of mediating the spatial organization of cells and cell bound proteins within a three dimensional collagen gel. Accordingly, ultrasound technology provides a mean for regulating the movement of extracellular matrix protein movement within an in vitro culture system. Spatial organization of extracellular matrix proteins, like fibronectin, in a collagen matrix enhances the extent of cell-mediated collagen remodeling. Controlling extracellular matrix remodeling within an in vitro culture system is important for promoting and enhancing the mechanical strength of the cultured tissue, a factor that is critical for engineering larger, more complex, three dimensional tissues than are currently available.

Any of the in vitro culture systems and the ultrasound exposure parameters described infra are suitable for use in accordance with this aspect of the present invention.

A third aspect of the present invention is directed to a method of inducing neovessel formation in an in vitro culture system. This method involves providing an in vitro culture system comprising a biological support material and endothelial cells, and placing the in vitro culture system in an ultrasound exposure chamber. The method further involves exposing the in vitro culture system to an ultrasound standing wave field under conditions effective to spatially organize endothelial cells, and incubating the in vitro culture system containing the spatially organized endothelial cells under conditions effective to induce neovessel formation.

In accordance with this aspect of the present invention, "neovessel formation" refers to the generation of any vascular structure including capillaries and blood vessels in the in vitro culture system. In accordance with this aspect of the invention, neovessel formation may result from neovascularization or angiogenic processes.

Accordingly, in a preferred embodiment of the present invention, the in vitro culture system includes vascular endothelial cells in combination with one or more tissue specific cell types. Suitable endothelial cells include primary endothelial cells (e.g., human umbilical vein endothelial cells) as well as endothelial cell lines. Also suitable for use in the present invention are endothelial progenitor cells, hematopoietic cells, and embryonic stem cells capable of endothelial cell differentiation. Preferably, the endothelial cells and tissue specific cells of the present invention are mammalian cells and more preferably the cells are human cells.

The in vitro culture system may further contain particles (e.g., nanoparticles, microparticles, microbubbles, etc.) that contain or carry endothelial cell specific growth factors and/or angiogenic growth factors to promote endothelial cell differentiation and neovessel formation. Suitable growth factors include, without limitation, FGF, bFGF, acid FGF (aFGF), FGF-2, FGF-4, EGF, PDGF, TGF-beta1, angiopoietin-1, angiopoietin-2, placental growth factor (PlGF), VEGF, PMA (phorbol 12-myristate 13-acetate), and the like.

The methods of the present invention can be adapted to any in vitro culture system known in the art. In fact, various in vitro culture systems have been developed for the generation of three dimensional engineered tissue construct and all are suitable for use in the method of the present invention. It is expected that application of the methods of the present invention to these systems will facilitate the vascularization of such tissue constructs resulting in the generation of more complex three dimensional tissues having expanded in vitro and, more importantly, having in vivo utility. Examples of suitable three dimensional tissue engineered constructs include, without limitation, oral tissue constructs (U.S. Patent Application Publication No. 20060171902 to Atala et al., which is hereby incorporated by reference in its entirety); cardiac constructs (U.S. Patent Application Publication No. 20080075750 to Akins and U.S. Pat. No. 5,885,829 to Mooney et al, which are hereby incorporated by reference in their entirety); embryonic brain tissue construct (U.S. Patent Application Publication No. 20060030043 to Ma, which is hereby incorporated by reference in its entirety); muscular construct (U.S. Patent Application Publication Nos. 2006019827 to Levenberg et al., 20060134076 to Bitar et al, and U.S. Pat. No. 6,537,567 to Niklason et al., which are hereby incorporated by reference in their entirety); stromal cell constructs (U.S. Pat. No. 4,963,489 to Naughton et al. and U.S. Patent Application Publication No. 2003007954 to Naughton et al., which are hereby incorporated by reference in their entirety); embryonic tissue constructs (U.S. Patent Application Publication No. 20050031598 to Levenberg et al., which is hereby incorporated by reference in its entirety); pancreatic constructs (U.S. Pat. No. 6,022,743 to Naughton et al., which is hereby incorporated by reference in its entirety); skin constructs (U.S. Pat. No. 5,266,480 to Naughton et al., which is hereby incorporated by reference in its entirety); filamentous tissue/ligament construct (U.S. Pat. No. 6,140,039 to Naughton et al., U.S. Pat. No. 6,840,962 to Vacanti et al., and now U.S. Pat. No. 6,737,053 to Goh et al., which are hereby incorporated by reference in their entirety); cartilage constructs (U.S. Pat. No. 5,902,741 to Purchio et al., which is hereby incorporated by reference in its entirety); vascular constructs (U.S. Pat. No. 6,455,311 to Vacanti, U.S. Pat. No. 7,112,218 to McAllister et al., and U.S. Pat. No. 7,179,287 to Wolfinbarger, which are hereby incorporated by reference in their entirety); kidney constructs (U.S. Pat. No. 5,516,680 to Naughton et al., which is hereby incorporated by reference in its entirety); uterine constructs (U.S. Patent Application Publication No. 20030096406 to Atala et al., which is hereby incorporated by reference in its entirety); and liver constructs (U.S. Pat. No. 5,624,840 to Naughton et al., which is hereby incorporated by reference in its entirety).

Any of the in vitro culture systems and the ultrasound exposure parameters described infra are suitable for use in accordance with this aspect of the present invention.

Another aspect of the present invention is directed to a vascularized engineered tissue construct made in accordance with the methods described herein. This vascularized engineered tissue construct has a three-dimensional thickness of at least 2 mm.

In accordance with this aspect of the present invention, the vascularized engineered tissue construct contains networks of microvessels having internal diameters of about 0.5 mm or less. These microvessels of the tissue construct form an "exchange" network that is capable of supplying nutrients and removing wastes from the new tissue. Upon transplantation of the vascularized tissue construct of the present invention, the tissue construct integrates or connects to host tissue either by inducing incoming vessels into the construct (i.e., angioinduction) and/or by allowing the construct vessels to meet the host vessles (i.e., inosculation).

Vascularized engineered tissue constructs generated in accordance with the present invention include, without limitation, a vascularized cardiac construct, muscular construct, a vascular construct, an esophageal construct, an intestinal construct, a rectal construct, an ureteral construct, a cartilaginous construct, a liver construct, a bladder construct, a kidney construct, a pancreatic construct, a skeletal construct, a filamentous/ligament construct, a lung construct, a neural construct, a bone construct, and a skin construct.

In one embodiment of the present invention, a three dimensional vascularized engineered cardiac tissue construct is generated. The cell types that may be used to generate a three dimensional cardiac construct may include, but are not limited to, cardiomyocytes, endocardial cells, cardiac adrenergic cells, cardiac fibroblasts, vascular endothelial cells, smooth muscle cells, stem cells, cardiac progenitor cells, and myocardial precursor cells. Depending on the application of the vascularized three dimensional cardiac construct and the type of cardiac tissue material that is desired, the above types of cells may be used independently or in combination. In one embodiment, the vascularized three dimensional cardiac construct may be composed of autologous primary tissue isolates from the heart of a patient. Alternatively, cells such as non-immunogenic universal donor cell lines or stem cells may be used.

In another embodiment of the present invention, a vascularized three dimensional engineered ligament construct is generated. The cell types that may be used to generate a three dimensional ligament construct may include, without limitation, tenocytes, ligamentum cells, fibroblasts, chondrocytes, and endothelial cells. These cells may be used independently or in combination and may be primary cells or derived from cell lines.

Vascularized tissue engineered constructs generated using the methods of the present invention have various in vitro and in vivo biomedical applications In one embodiment, a tissue engineered construct of the present invention is employed in an in vitro method of screening a test agent. In vitro screening may include, without limitation, toxicological testing of an agent, drug discovery, and biological and chemical warfare detection. Suitable drugs or agents to be tested using the tissue constructs of the present invention include cytotoxic agents, pharmaceutical agents, growth factors, etc. In accordance with this aspect of the invention, a test agent is contacted with a vascularized tissue construct of the present invention and one or more biological endpoints is assayed. Suitable biological endpoints to be assayed include, without limitation, carcinogenicity, cell death, cell proliferation, gene expression, protein expression, cellular metabolism, and any combination thereof. Because cellular spatial organization and neovascularization can be induced and controlled in the in vitro culture system of the present invention, the resulting vascularized engineered tissue construct better replicates the in vivo tissue architecture and cellular microenvironment, providing an improved in vitro test model. Use of vascularized engineered tissue constructs of the present invention provides an attractive alternative to the use of animal models for testing and screening agents.

In another embodiment, the vascularized tissue engineered constructs generated using the methods of the present invention are suitable for implantation and transplantation into a recipient subject in need of tissue repair or tissue replacement. The method involves selecting a subject that is in need of tissue repair or tissue replacement and implanting a suitable vascularized engineered tissue construct of the present invention into the selected subject. In accordance with this aspect of the present invention, a suitable subject is any animal, preferably a mammal, more preferably, a human subject.

The vascularized engineered tissue constructs of the present invention may be used to replace or augment existing tissue, to introduce new or altered tissue, to modify artificial prostheses, or to join together biological tissues or structures. For implantation or transplantation in vivo, either the cells obtained from the in vitro culture system or, more preferably, the entire vascularized three dimensional engineered tissue construct is implanted, depending on the type of tissue involved. In accordance with this aspect of the invention, it is desirable to use allogeneic cells in the in vitro culture system. Allogeneic cells or tissue originate from or is derived from a donor of the same species as the recipient.

The following examples illustrate various methods for compositions in the treatment method of the invention. The examples are intended to illustrate, but in no way limit, the scope of the invention.

EXAMPLES

Materials and Methods for Examples 1-7

Experimental Set-Up. The experimental set-up used for all USWF exposures is depicted in FIG. 1A. A plastic exposure tank (36×20×18 cm) was filled with degassed, deionized water at room temperature. The acoustic source consisted of a 1 MHz unfocused transducer, fabricated from a 2.5 cm diameter piezoceramic disk. The transducer was mounted on the bottom of the water tank. The signal driving the transducer was generated by a waveform generator (Model 33120A, Hewlett Packard, Palo Alto, Calif., USA), RF power amplifier (Model 2100L, ENI, Rochester, N.Y., USA), and an attenuator (Model 837, Kay Elemetrics Corp., Lincoln Park, N.J., USA). Samples were contained within the wells of a modified silicone elastomer-bottomed cell culture plate (BioFlex® culture plates, FlexCell International Corporation, Hillsborough, N.C., USA). These sample holders were mounted to a three-axis positioner (Series B4000 Unislide, Velmex Inc., East Bloomfield, N.Y., USA) to allow precise control over their location within the sound field. The air interface above the samples was used as the acoustic reflector to generate an USWF within the sample volume.

Figure 1B:
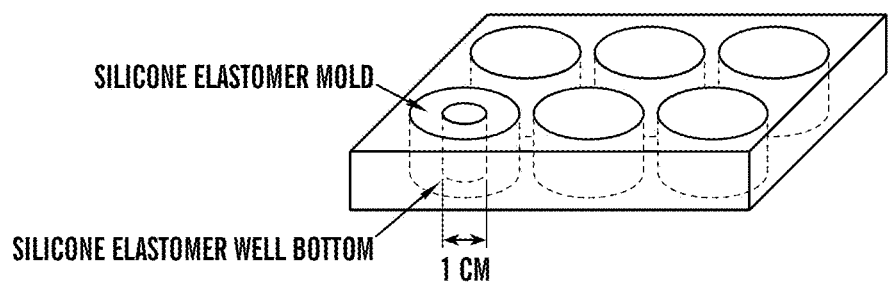

Sample Holder Preparation. The BioFlex® culture plates used as sample holders for these investigations are depicted in FIG. 1B. They were modified from the manufacturer's form by reducing the diameter of 3 wells per plate from 4 cm to 1 cm using Sylgard® 184 Silicone Elastomer (Dow Corning Corporation, Midland, Mich., USA). Through this modification, the diameter of the sample was comparable in size to the width of the ultrasound beam. The two-part silicone elastomer was mixed in a 10:1 ratio as recommended by the manufacturer's instructions. The solution was degassed at room temperature using a vacuum chamber (Model 5830, National Appliance Company, Portland, Oreg., USA) and was subsequently poured around 1 cm diameter Teflon® mandrels (Dupont, Wilmington, Del., USA) that were placed at the center of the 3 wells of interest. Following curing of the silicone elastomer at 20° C. for 48 hr, the mandrels were carefully removed to leave a 1 cm diameter sample space within 3 wells of each BioFlex® culture plate (FIG. 1B).

Attenuation Measurements. The acoustic attenuations of the silicone elastomer well bottom of the BioFlex® plates, the Sylgard® 184 Silicone Elastomer, and standard tissue culture polystyrene (Corning/Costar, Cambridge, Mass., USA) were measured using an insertion loss technique. Using the water tank set-up, each material was inserted into the acoustic path between the unfocused 2.5 cm diameter, 1 MHz transducer and a hydrophone (either a bilaminar PVDF membrane hydrophone (Marconi Research Center, Chelmsford, England) or a ceramic-based needle hydrophone (Model HNC-0400, Onda Corporation, Sunnyvale, Calif., USA)). Peak positive and peak negative pressure amplitudes were measured using the hydrophone and a digital oscilloscope (Model 9310AM, LeCroy, Chestnut Ridge, N.Y., USA) in the presence and absence of each material for various source amplitudes. The thickness of each material was measured using calipers. The acoustic attenuation coefficient (in dB/MHz/cm) was calculated for each material.

Absorption/Heating Measurements. The acoustic absorption coefficient of Sylgard® 184 Silicone Elastomer was measured using a thermocouple technique. Briefly, a 50 μm copper-constantan thermocouple was embedded in a sample of Sylgard® 184 Silicone Elastomer. Using the water tank set-up, the active element of the embedded thermocouple was positioned at the focus of a 1 MHz transducer fabricated from a 3.8 cm diameter plane, piezoceramic disk cemented to the back of a plano-concave lens. A laboratory thermometer (Model BAT-4, Bailey Instruments Co. Inc., Saddle Brook, N.J., USA) and digital oscilloscope were used to monitor the thermocouple output for various pulsing parameters and exposure amplitudes. For each exposure condition, the initial rate of temperature rise in the sample and the spatial peak temporal average intensities ($I_{spta}$) were measured and used to calculate the absorption coefficient. The calculated absorption coefficients from each exposure condition were averaged to determine the acoustic absorption coefficient (in dB/cm) of Sylgard® 184 Silicone Elastomer at 1 MHz.

Temperature changes in the collagen/cell samples were also monitored during USWF exposure using a 50 μm copper-constantan thermocouple. Thermocouple output was monitored using a digital laboratory thermometer (Model BAT-12, Physitemp Instruments Inc., Clifton, N.J., USA), sensitive to changes of 0.1° C., over the duration of USWF exposures.

Acoustic Field Measurements. Using the water tank set-up, axial spatial distributions of pressure from the 1 MHz, 2.5 cm diameter unfocused transducer were measured under USWF exposure conditions in both the presence and absence of the sample holder. The Onda ceramic-based needle hydrophone, connected to a three-axis positioner, and a digital oscilloscope were used to measure the acoustic pressure. The sample holder was placed in the far-field with the well bottoms situated at an axial distance of 12.2 cm from the transducer. Axial spatial distributions of pressure were measured through a 0.5 cm distance below the air interface in 0.1 mm intervals. A sinusoidal pulse of 50 μs duration was employed and peak positive pressures were measured for each position. The 0.5 cm distance approximates the height of the collagen samples used in these investigations. At the axial distance of 12.2 cm from the transducer, the −6 dB transaxial beamwidth in the free field was measured to be 1.2 cm.

Acoustic Field Calibrations. Prior to each experiment, the acoustic field was calibrated using either the Marconi PVDF membrane hydrophone or the Onda ceramic-based needle hydrophone under traveling wave conditions. Hydrophones were calibrated regularly using the steel sphere radiometer technique (Dunn et al., "A Primary Method for the Determination of Ultrasonic Intensity With Elastic Sphere Radiometer," *Acustica* 388:58-61 (1977), which is hereby incorporated by reference in its entirety). Acoustic pressure was measured in the far-field at an axial distance of 12.2 cm from the transducer (where samples were located during USWF exposure). Coordinates from the exposure site to a fixed pointer were determined using the three-axis positioner and were used to position the center of the lower, left-hand well of the sample holder at the exposure site (bottom of the well was 12.2 cm from the transducer). Some water was removed from the tank such that the sample holder was located at the exposure site without full submersion.

Cell Culture. Fibronectin-null mouse embryonic myofibroblasts (obtained from Dr. Jane Sottile, University of Rochester) were used for all experiments. These cells do not produce fibronectin and have been adapted to grow under serum-free conditions (Sottile et al., "Fibronectin Matrix Assembly Enhances Adhesion-dependent Cell Growth," *J Cell Sci* 111:2933-43 (1998), which is hereby incorporated by reference in its entirety). Cells were routinely cultured in a 1:1 mixture of AimV (Invitrogen, Carlsbad, Calif., USA) and Cellgro (Mediatech, Herndon, Va., USA) on tissue culture dishes pre-coated with collagen type-I. These media do not require serum supplementation. Thus, no source of fibronectin is present during routine culture. On the day of USWF exposure, fibronectin-null cells were harvested from monolayer culture by treatment with 0.08% trypsin (Invitrogen) and 0.5 mM EDTA in PBS. Trypsin activity was neutralized with 2 mg/ml soybean trypsin inhibitor (STI; Sigma, St. Louis, Mo.). Cells were washed one time with 1 mg/ml STI in PBS and were then resuspended in a 1:1 mixture of AimV/Cellgro.

Collagen Solution Preparation. A neutralized type-I collagen solution was prepared on ice by mixing collagen type-I, isolated from rat tail tendons, with 2× concentrated Dulbecco's modified Eagle's medium (DMEM; Invitrogen) and 1× DMEM containing HEPES so that the final mixture consisted of 0.8 mg/ml collagen and 1×DMEM (Hocking et al., "Stimulation of Integrin-mediated Cell Contractility by Fibronectin Polymerization," *J Biol Chem* 275:10673-82 (2000), which is hereby incorporated by reference in its entirety). Both the 1× and 2×DMEM media were degassed in a vacuum chamber for 30 min under sterile conditions prior to incorporation into the collagen mixture.

USWF Exposures. Fibronectin-null cells were added to aliquots of neutralized type-I collagen solutions on ice at various final concentrations immediately prior to USWF exposure. Aliquots (400 µl) of the collagen/cell solution were then loaded into two of the 1 cm diameter Sylgard® 184 Silicone Elastomer molded wells of the BioFlex® plate. For "no-cell" samples, an equal volume of AimV/Cellgro was added in place of fibronectin-null cells and aliquots were loaded into a third well. The collagen/cell solution in the left-hand well of each plate was exposed to a 1 MHz, continuous wave USWF for 15 min at room temperature. The two other samples in the plate (right-hand side) served as sham control wells that were treated exactly as the exposed sample but were not exposed to the USWF. The 15 min exposure duration was sufficient to promote collagen polymerization at room temperature. Following USWF exposure, collagen gels were incubated for 1 hr at 37° C. and 8% $CO_2$ to allow for complete collagen polymerization. An equal volume (400 µl) of DMEM was then added to wells containing collagen gels. In some experiments, collagen/cell and collagen/no-cell solutions were incubated for 1 hr at 37° C. and 8% $CO_2$ in the sample holders to allow collagen polymerization before USWF exposure.

Cell Viability Assay. Thiazolyl blue tetrazolium bromide (MTT) was used to assess cell viability (Mosmann T., "Rapid Colorimetric Assay for Cellular Growth and Survival: Application to Proliferation and Cytotoxicity Assays," *J Immunol Methods* 65:55-63 (1983), which is hereby incorporated by reference in its entirety). At various time points after USWF exposure, collagen gels were incubated with 5.3 mM MTT (USB Corporation, Cleveland, Ohio, USA) for 4 hr at 37° C. and 8% $CO_2$. Gels were then digested with 0.77 mg/ml collagenase (from *Clostridium histolyticum*, type-I, Sigma) and formazan crystals were dissolved using acidified isopropanol (0.04 N HCl). Absorbance measurements at 570 nm and 700 nm (background) were determined using a spectrophotometer. MTT absorbance was calculated by subtracting background absorbance values and non-specific reduction of MTT in no-cell gels from the 570 nm readings. There was a linear relationship between cell number and MTT absorbance. This assay is sensitive to differences of 5000 cells and greater.

Collagen Gel Contraction Assays. The extent of collagen gel contraction was determined using two established methods. For volumetric gel contraction assays, gels were scored around their edges to form free-floating gels in the wells. After an additional 20 hr of incubation at 37° C. and 8% $CO_2$, the gels were removed from the wells and weighed (Model B303, Mettler Toledo, Columbus, Ohio, USA). Volumetric collagen gel contraction was calculated as a decrease in gel weight as compared to the control, no-cell gel weight (Hocking et al., "Stimulation of Integrin-mediated Cell Contractility by Fibronectin Polymerization," *J Biol Chem* 275:10673-82 (2000), which is hereby incorporated by reference in its entirety). For radial gel contraction assays, gel diameters were measured using a 10× inspection microscope equipped with a calibrated eyepiece micrometer. Two measurements were recorded for each gel and averaged to calculate gel diameter. Investigators measuring diameters were blinded to exposure conditions. Radial collagen gel contraction was calculated as a decrease in gel diameter as compared to the original gel diameter of 1 cm (Tingstrom et al., "Regulation of Fibroblast-mediated Collagen Gel Contraction by Platelet-derived Growth Factor, Interleukin-1 Alpha and Transforming Growth Factor-beta1," *J Cell Sci* 102:315-22 (1992), which is hereby incorporated by reference in its entirety).

Soluble Fibronectin Binding. Fibronectin-null cells in suspension ($2 \times 10^7$ cell/ml) were incubated with 100 µg/ml of Alexa Fluor® 488-labeled human, plasma-derived fibronectin (FN-488; labeled according to manufacturer's instructions) in the presence of 1 mM $MnCl_2$ for 30 min at room temperature (Akiyama et al., "The Interaction of Plasma Fibronectin With Fibroblastic Cells in Suspension," *J Biol Chem* 260:4492-500 (1985) and Mastrangelo et al., "Amino Acid Motifs for Isolated Beta Cytoplasmic Domains to Regulate 'in Trans' Beta-1 Integrin Conformation and Function in Cell Attachment," *J Cell Sci* 112:217-29 (1999), which are hereby incorporated by reference in their entirety). Cells were washed twice with AimV/Cellgro to remove unbound fibronectin and were then added to neutralized type-I collagen solutions and exposed to an USWF as described above. In other experiments, 10 µg/ml of FN-488 was added to neutralized type-I collagen solutions in the absence of cells and exposed to an USWF as described above.

Microscopy. One hour after USWF exposure, cell-embedded collagen gels were examined using an Olympus IX70 inverted microscope (Center Valley, Pa., USA) with a 4× phase-contrast objective and were photographed using a digital camera (Spot RT Slider, Model 2.3.1, Diagnostic Instruments Inc., Sterling Heights, Mich., USA). FN-488 was visualized using epifluorescence microscopy. Gels were flipped on their side to visualize cell bands through the height of the cylindrical sample. For volumetric collagen gel contraction experiments, gels were imaged after obtaining weight data. Image-Pro Plus software (Media Cybernetics, Bethesda, Md., USA) was used to measure the linear distance between fibronectin-null cell bands within collagen gels. Pixel distance was converted to micron values using a micrometer calibration. A total of 10 distances were measured on each of 20 different images collected from 3 different experiments.

To visualize type-I collagen fibers, cell-embedded collagen gels were examined using second-harmonic generation microscopy (Freund et al., "Second-harmonic Microscopy of Biological Tissue," *Opt Lett* 11:94-6 (1986); Roth et al., "Second Harmonic Generation in Collagen," *J Chem Phys* 70:1637-43 (1979); and Williams et al., "Interpreting Second-Harmonic Generation Images of Collagen I Fibrils," *Biophys J* 88:1377-86 (2005), which are hereby incorporated by reference in their entirety). One hour after USWF exposure, gels were fixed in 4% paraformaldehyde for 1 hr at room temperature. Second-harmonic generation microscopy was performed using an Olympus Fluoview 1000 AOM-MPM microscope equipped with a 25×, 1.05 NA water immersion lens (Olympus). Samples were illuminated with 780 nm light generated by a Mai Tai HP Deep See Ti:Sa laser (Spectra-Physics, Mountain View, Calif., USA) and the emitted light was detected with a photomultiplier tube using a bandpass filter with a 390 nm center wavelength (Filter FF01-390/40-25, Semrock, Inc., Rochester, N.Y., USA). Fibronectin-null cells were simultaneously visualized using a second bandpass filter with a 519 nm center wavelength (Filter BA 495-540 HQ from MPFC1, Olympus) by exploiting the intrinsic auto-fluorescence of cells (Monici M., "Cell and Tissue Autofluorescence Research and Diagnostic Applications," *Biotechnol Annu Rev* 11:227-56 (2005), which is hereby incorporated by reference in its entirety). Cell-embedded collagen gels were photographed using a CMOS digital camera (Moticam 1000, Motic, China).

Statistical Analyses. Data are presented as the mean□±SEM. Statistical comparisons between USWF-exposed and sham experimental conditions were performed using either the Student's t test for paired samples or one-way analysis of variance in GraphPad Prism software (La Jolla, Calif., USA). Differences were considered significant for p values <0.05.

Example 1

Experimental Set-Up for Ultrasound Exposures

To investigate the effects of ultrasonic mechanical forces on the promotion of angiogenesis, an ultrasound (US) exposure system was developed in which cells and 3D tissue constructs are subjected to an ultrasound traveling wave field (UTWF) or an ultrasound standing wave field (USWF) (FIG. 1A). Samples are contained within the wells of a modified silicone elastomer-bottomed cell culture plate (FIG. 1B). UTWF are created by minimizing reflections at the sample/air interface with a rubber absorber. USWF are produced by removing the rubber absorber such that the air interface promotes the interference of incident and reflected waves (Blackstock DT, FUNDAMENTALS OF PHYSICAL ACOUSTICS, (Wiley & Sons, 2000), which is hereby incorporated by reference in its entirety). No significant differences in UTWF or USWF are found in the presence of the sample holder compared to without the holder, indicating that the experimental set-up will not interfere with the sound field.

The ultrasound attenuation of standard polystyrene multi-well tissue culture plates was measured to be 4.5±0.7 □dB/MHz/cm (n=3). Due to the significant attenuation of the sound field by these polystyrene plates, the use of silicone elastomer-bottomed plates was investigated as an alternative sample holder for these studies. The acoustic attenuation of the silicone elastomer well bottom (thickness=1 mm) of the BioFlex® plates was measured to be only 0.6±0.4 dB/MHz/cm (n=3) indicating that there is negligible attenuation (0.06 dB at 1 MHz) of the sound field due to the presence of the BioFlex® sample holders.

The ultrasound attenuation of the Sylgard® 184 Silicone Elastomer molding material was measured to be 2.4±0.04 dB/MHz/cm (n=3). Sound absorption at 1 MHz (1.4±0.03 dB/cm; n=3) was found to contribute to ~60% of this attenuation. Thermocouple measurements monitoring sample temperature during USWF exposure indicated that collagen/cell sample temperatures never exceeded that of room temperature. Therefore, the BioFlex® plates modified with the Sylgard® 184 Silicone Elastomer molds were chosen as sample holders for these investigations because they did not significantly interfere with the sound field.

Example 2

Characterization of Ultrasound Fields

USWF and traveling wave fields were measured in a water tank and within the sample space using the set-up described above. Resulting spatial distributions of pressure are illustrated below in FIGS. 2A-2D. An unfocused, 1 MHz, 1 inch diameter, piezoelectric transducer was used to produce the US field and a needle hydrophone was used to measure the acoustic pressure.

Figure 2A:
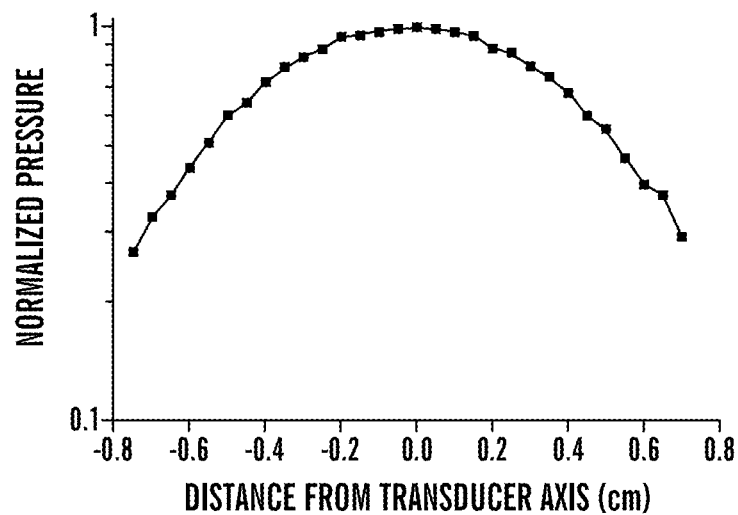
FIGS. 2A-2D are graphs showing the ultrasound beam patterns in free field and sample space. Transaxial spatial distributions in pressure were measured in both the free field (FIG. 2A) and within the 1 cm diameter sample space (FIG. 2B). Data are plotted as normalized pressure versus spatial location. The calculated −3 dB and −6 dB beam widths were 0.8 cm and 1.2 cm in the free field. The axial spatial distribution in pressure within an USWF (FIGS. 2C-2D) was measured in 0.2 mm intervals through a 1 cm distance below the air interface in both the free field (FIG. 2C) and sample space (FIG. 2D). Peak positive pressures were measured for each position. The distance between pressure nulls was calculated as the distance between pressure minima and was approximately the expected half-wavelength spacing for 1 MHz sound in water (0.75 mm).
Figure 2B:
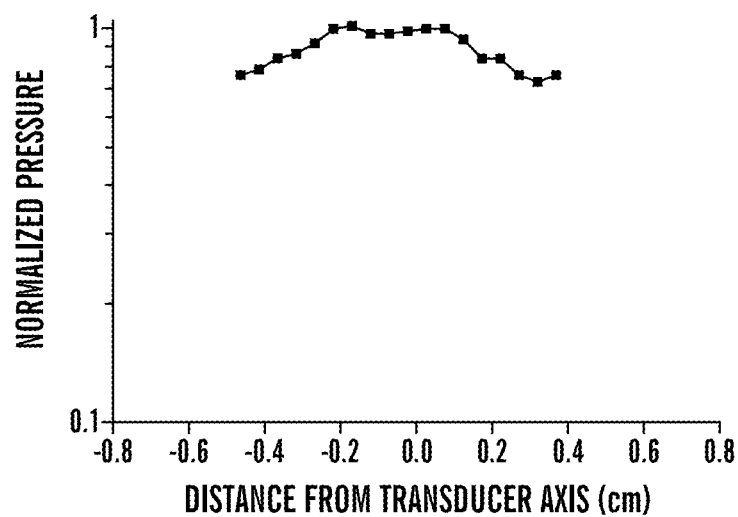
Figure 2C:
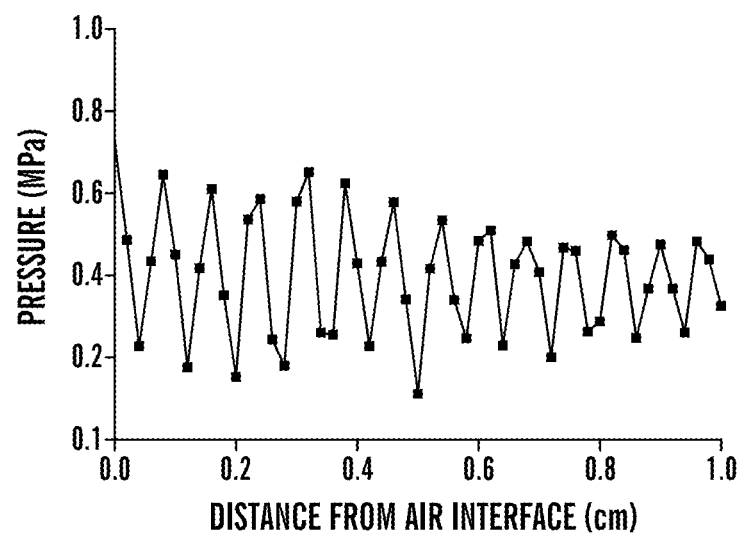
Figure 2D:
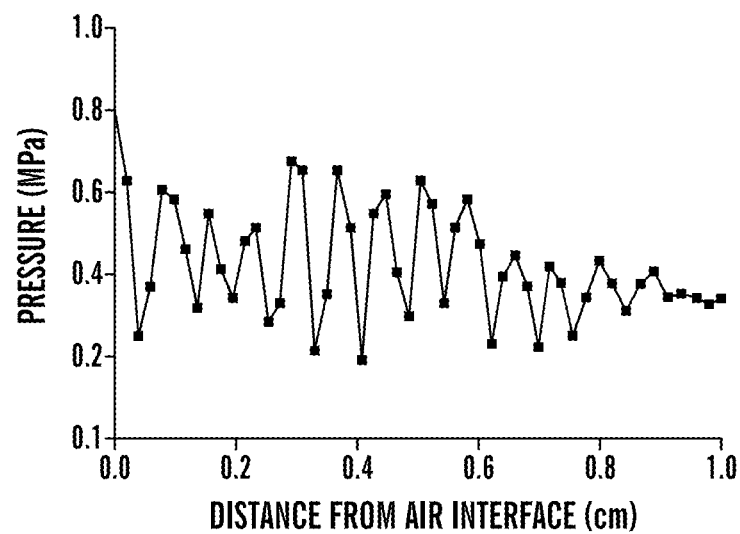

For traveling wave fields, transaxial spatial distributions in pressure were measured in the far field, 12.2 cm from the transducer. In the absence of the sample holder, −3 dB and −6 dB beam widths were 0.8 cm and 1.2 cm, respectively (FIG. 2A). The beam pattern within the sample space was not significantly altered from the free field pattern indicating that the sample holder does not interfere with sound propagation (FIG. 2B). The −3 dB beam width remained 0.8 cm, but the −6 dB beam width could not be calculated, indicating that samples will be exposed to a relatively uniform pressure distribution within the −6 dB beam width.

For standing wave fields, axial spatial distributions in pressure were measured through a 1 cm distance, starting at the air interface. In both the absence (FIG. 2C) and presence (FIG. 2D) of the sample holder, beam patterns exhibited characteristic pressure maxima and minima indicating that the sample holder did not interfere with the development of the USWF. A distance of 0.8 mm separated pressure minima in both beam patterns, a finding that is consistent with the expected half-wavelength spacing between the pressure nodes in an USWF at 1 MHz.

Example 3

USWF Control of the Spatial Arrangement of Cells Within a 3D Tissue Construct

Figures 3A, 3B, 3C:
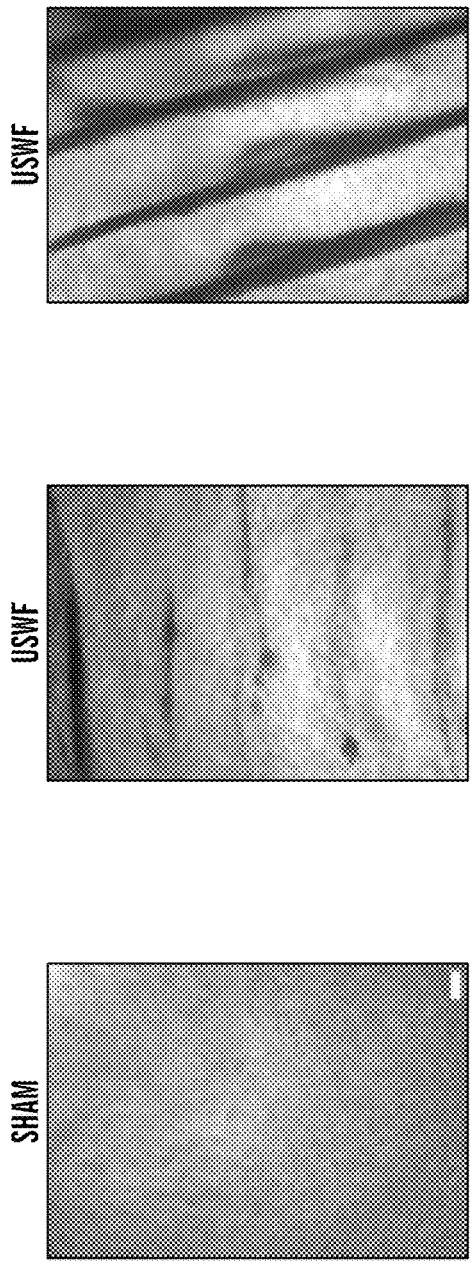
FIGS. 3A-3C illustrate ultrasound standing wave fields (USWF) induced changes in the spatial organization of cells in 3D collagen gels. Fibronectin-null (FN−/−) myofibroblasts (MF) at $2\times10^5$ c/ml (FIGS. 3A and 3B) or $4\times10^6$ c/ml (FIG. 3C), suspended in a collagen I solution (0.8 mg/ml), were exposed to an USWF using a 1 MHz continuous wave (CW) sinusoidal signal for 15 min with an incident pressure amplitude of 0.1 MPa. Representative phase-contrast images, from one of at least two experiments performed in duplicate, show dark bands of cells in USWF-exposed gels (FIGS. 3B and 3C) that are absent in sham gels (FIG. 3A) where a homogeneous cell distribution is observed. Scale bar, 200 μm.

The organization of endothelial cells into multicellular assemblies affects angiogenic endothelial cell behaviors (Korff et al., "Integration of Endothelial Cells in Multicellular Spheroids Prevents Apoptosis and Induces Differentiation," *The Journal of Cell Biology* 143(5):1341-1352 (1998) and Ino et al., "Application of Magnetic Force-Based Cell Patterning for Controlling Cell-Cell Interactions in Angiogenesis," *Biotechnology and Bioengineering* 102(3): 882-890 (2009), which are hereby incorporated by reference in their entirety). Exposure of cell suspensions to USWF can result in cellular aggregation at areas of minimum acoustic pressure (the pressure nodes) (Dyson et al., "The Production of Blood Cell Stasis and Endothelial Damage in the Blood Vessels of Chick Embryos Treated with Ultrasound in a Stationary Wave Field," *Ultrasound in Medicine and Biology* 1:133-148 (1974), which is hereby incorporated by reference in its entirety). An USWF acoustic radiation force is largely responsible for this cell movement (Coakley et al., "Cell Manipulation in Ultrasonic Standing Wave Fields," *Journal of Chemical Technology and Biotechnology* 44:43-62 (1989), which is hereby incorporated by reference in its entirety). To determine if USWF radiation forces could manipulate cell organization in 3D collagen gels, fibronectin-null myofibroblasts (FN−/− MF), suspended in unpolymerized type-I collagen solutions, were either exposed to, or not exposed to (sham samples), a 1 MHz, continuous wave (CW) USWF using the experimental set-up shown in FIG. 1A. Collagen solutions were allowed to polymerize during the 15 min exposure to maintain the US-induced cell distribution after removal of the pressure field (Saito et al., "Composite Materials with Ultrasonically Induced Layer or Lattice Structure," *Jpn Journal of Applied Physics* 38:3028-3031 (1999); Saito et al., "Fabrication of a Polymer Composite with Periodic Structure by the Use of Ultrasonic Waves," *Journal of Applied Physics* 83(7):3490-3494 (1998); Gherardini et al., "A New Immobilisation Method to Arrange Particles in a Gel Matrix by Ultrasound Standing Waves," *Ultrasound in Medicine and Biology* 31(2):261-272 (2005); and Gherardini et al., "A Study of the Spatial Organization of Microbial Cells in a Gel Matrix Subjected to Treatment with Ultrasound Standing Waves," *Bioseparation* 10:153-162 (2002), which are hereby incorporated by reference in their entirety). Cell distribution was then analyzed using phase-contrast microscopy (FIGS. 3A-3C). FN−/− MF do not produce fibronectin and are grown in serum-free conditions (Sottile et al., "Fibronectin Matrix Assembly Enhances Adhesion-Dependent Cell Growth," *Journal of Cell Science* 111:2933-2943 (1998), which is hereby incorporated by reference in its entirety). As such, these cells were chosen for the initial studies to differentiate between the effects of USWF on the localization of cells and the extra-cellular matrix protein fibronectin. Gels polymerized in the presence of the USWF showed a distinct banded pattern, characterized by the localization of cells to the pressure nodes of the USWF (FIGS. 3B-3C), while sham samples exhibited a homogeneous cell distribution (FIG. 3A). The mean of the measured distance between cell bands was 657±15 µm. This is consistent with the expected half-wavelength spacing of 750 µm between pressure nodal planes in an USWF generated with a 1 MHz source. Increasing the initial concentration of cells in the collagen solutions leads to the formation of denser cell bands at the nodal planes (compare FIGS. 3B and 3C). These data indicate that an USWF can spatially organize cells within 3D collagen gels, and that the extent of the banded pattern of cells is dependent on cell concentration.

Figure 4:
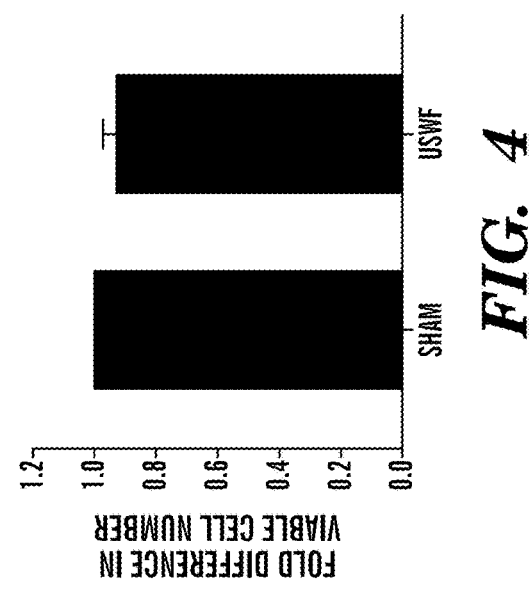
FIG. 4 is a graph showing that USWF exposure does not affect cell viability. Fibronectin-null myofibroblasts ($2\times10^5$ c/ml) suspended in a collagen I solution (0.8 mg/ml) were exposed to an USWF using a 1 MHz CW sinusoidal signal for 15 min with an incident pressure amplitude of 0.1 MPa. Following a 20 hr incubation period at 37° C. and 8% $CO_2$, cell-embedded collagen gels were incubated with MTT for 4 hrs, digested with collagenase, and formazen crystals were dissolved in acidified isopropanol to measure the absorbance at 570 nm and 700 nm (background) for quantification of viable cell number. Data from four experiments were normalized to sham average absorbance values±SEM.

In supplementary experiments, the MTT assay (Mosmann T., "Rapid Colorimetric Assay for Cellular Growth and Survival: Application to Proliferation and Cytotoxicity Assays," *Journal of Immunological Methods* 65(1-2):55-63 (1983), which is hereby incorporated by reference in its entirety) was used to show that USWF exposure did not adversely affect cell viability (FIG. 4). These findings indicate that USWF can noninvasively alter the spatial organization of cells within a 3D collagen gel without affecting cell viability.

To estimate the magnitude of radiation force exerted on the cells in the applied USWF, Equation 1 was used to calculate the maximum $F_{rad}$. The acoustic exposure parameters and the physical properties of the cells and the suspending collagen medium used for the calculation are listed in Table 1. Results of this calculation indicated that the cells were subjected to a maximum radiation force of approximately 2.2 pN.

TABLE 1

Parameters used for calculation of primary acoustic radiation force ($F_{rad}$) using Equation 1

| Parameters (units) | Numerical Value | Source/Reference |
|---|---|---|
| $P_o$ (MPa) | 0.2 | Hydrophone measurement |
| V (µm³) | 904.8 (cells) | Assuming spherical particles |
| | 4.2 × 10⁻⁶ (FN) | |
| r (µm) | 6 (cells) | cell radius measured for |
| | 0.01 (FN) | rounded fibronectin-null cells in suspension; FN radius (Vuillard et al. 1990) |
| $\beta_o$ (1/Pa) | 4.44 × 10⁻¹⁰ | Calculation from $\beta = 1/c^2\rho$ |
| $\beta_p$ (1/Pa) | 4.07 × 10⁻¹⁰ (cells) | |
| | 3.12 × 10⁻¹⁰ (FN) | |
| $c_o$ (m/s) | 1500 | Assuming collagen media |
| $\rho_o$ (kg/m³) | 1000 | has properties of water |
| λ (µm) | 1500 | at room temperature |
| f (MHz) | 1 | Chosen frequency for these studies |
| φ | 0.132 (cells) | Using Equation 2 |
| | 0.581 (FN) | |
| $c_p$ (m/s) | 1529 (cells) | cell value (Taggart et al. 2007); |
| | 1540 (FN) | FN value assumed to be sound speed in human soft tissue (Bamber 1998) |
| $\rho_p$ (kg/m³) | 1050 (cells) | cell value assumed to be |
| | 1350 (FN) | dominated by cytoplasm taken as low concentration saline (Baddour et al. 2005); FN value (Fischer et al. 2004) |
| z (µm) | 0-750 | axial distance between 2 pressure nodal planes (λ/2) |
| $F_{rad}$ max (pN) | ±2.2 (cells) | Calculated using Equation 1 |
| | ±4.5 × 10⁻⁸ (FN) | at z = λ/8 and 3λ/8 |

References cited in Table 1 which are hereby incorporated by reference in their entirety: Baddour et al., "High-Frequency Ultrasound Scattering from Microspheres and Single Cells," *J Acoust Soc Am* 117: 934-43 (2005); Bamber JC, *Ultrasonic Properties of Tissues*, in ULTRASOUND IN MEDICINE 57-88 (1998); Fischer et al., "Average Protein Density is a Molecular-Weight-Dependent Function:" Protein Sci 13: 2825-8 (2004); Taggart et al., "Ultrasonic Characterization of Whole Cells and Isolated Nuclei," *Ultrasound Med Biol* 33: 389-401 (2007)

Example 4

USWF Radiation Forces Control Soluble FN Organization Within 3D Constructs

Successful tissue engineering depends upon the stimulation of key cell functions, including cell proliferation, migration and differentiation. These processes are influenced by a variety of soluble and insoluble factors, including growth factors, cytokines, and extracellular matrix proteins (Langer and Vacanti, "Tissue Engineering," *Science* 260:920-6 (1993), which is hereby incorporated by reference in its entirety). Concentrating stimulatory proteins to the cell banded areas of collagen gels may stimulate cell function. The extracellular matrix protein, fibronectin, stimulates cell growth, migration, and contractility (Hocking et al., "Stimulation of Integrin-Mediated Cell Contractility by Fibronectin Polymerization," *J Biol Chem* 275:10673-82 (2000); Hocking and Chang, "Fibronectin Polymerization Regulates Small Airway Epithelial Cell Migration," *Am J Physiol Lung Cell Mol Physiol* 285:L169-L79 (2003); Sottile et al., "Fibronectin Matrix Assembly Enhances Adhesion-Dependent Cell Growth," *J Cell Sci* 111:2933-43 (1998), which are hereby incorporated by reference in their entirety).

Figure 5A:
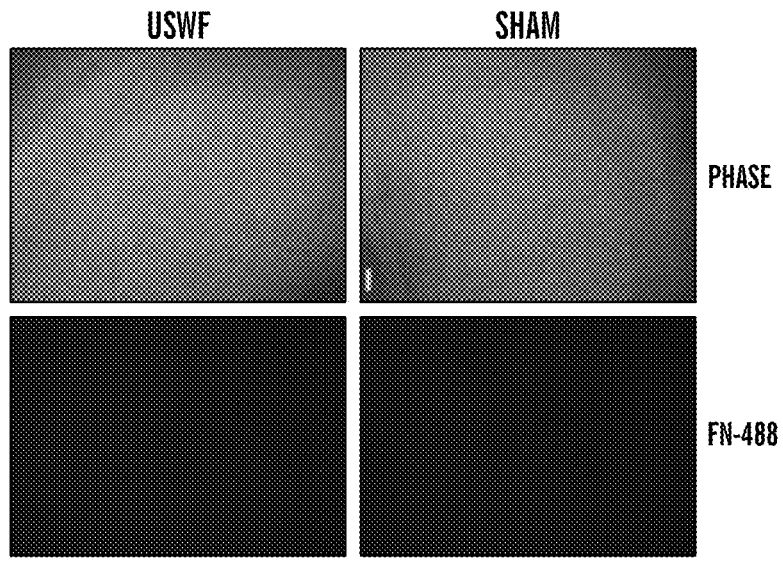
FIGS. 5A-5B are photomicrographs showing the spatial localization of soluble fibronectin (FN) in 3D collagen gels with and without USWF exposure. Fluorescently labeled fibronectin (FN-488; 10 μg/ml) was added to collagen I solutions in the absence of cells, and exposed to an USWF using a 1 MHz CW sinusoidal signal for 15 min with an incident pressure amplitude of 0.1 MPa (FIG. 5A, bottom panels). Fibronectin distribution was analyzed using phase-contrast (FIG. 5A; left panel) and fluorescent microscopy (FIG. 5A; right panel). Fibronectin-null myofibroblasts in suspension were incubated with 100 μg/ml FN-488 in the presence of 1 mM $MnCl_2$. Cells were washed twice to remove unbound FN and were then added to unpolymerized collagen I solutions ($4\times10^6$ c/ml) for exposure to the aforementioned USWF. Cell and FN distribution were analyzed using phase-contrast (FIG. 5B, left panel) and fluorescent microscopy (FIG. 5B, right panel), respectively. Representative images are shown. Scale bar, 200 μm
Figure 5B:
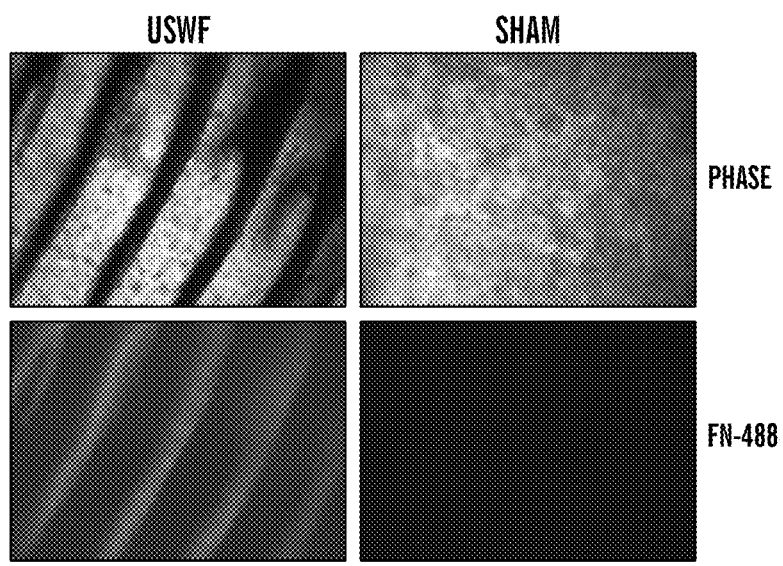

USWF radiation force theory predicts that small protein molecules such as fibronectin will not localize to the pressure nodes of an USWF (Coakley et al., "Cell Manipulation in Ultrasonic Standing Wave Fields," *Journal of Chemical Technology and Biotechnology* 44:43-62 (1989) and Whitworth et al., "Particle Column Formation in a Stationary Ultrasonic Field," *Journal of the Acoustical Society of America* 91(1):79-85 (1992), which are hereby incorporated by reference in their entirety). Using the aforementioned experimental set-up and USWF exposure conditions, this idea was confirmed by including Alexa488-labeled, human, plasma-derived fibronectin (FN-488) in unpolymerized collagen solutions and allowing polymerization to occur during USWF exposure. Fluorescent microscopy images show a homogeneous distribution of soluble fibronectin remaining after USWF exposure (FIG. 5A bottom left panel). To facilitate localization of fibronectin to cell-aggregated areas of collagen gels, soluble FN-488 molecules were bound to FN-/-MF prior to USWF exposure. Fluorescent microscopic analysis shows a co-localization of fibronectin molecules to USWF-induced cell bands within the collagen gels (FIG. 5B bottom right panel) indicating that USWF radiation forces can noninvasively control the organization of cell-bound fibronectin within 3D tissue constructs. As such, the mechanical forces associated with ultrasound can influence extracellular matrix (ECM) organization and thus have the potential to affect endothelial cell functions essential to the angiogenic process.

Example 5

USWF-Induced Cell Organization Enhances Cell-Mediated Collagen Gel Contraction

Figure 6A:
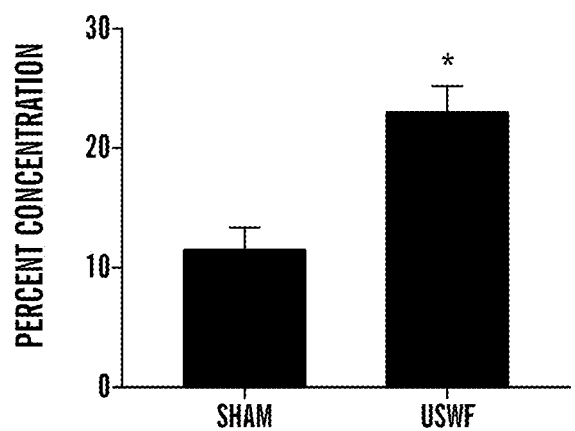
FIGS. 6A-6D show USWF induced cellular organization enhances cell-mediated collagen gel contraction. Fibronectin-null myofibroblasts ($2\times10^5$ c/ml) were suspended in a collagen I solution (FIGS. 6A and 6B) or embedded in polymerized collagen I gels (FIGS. 6C and 6D) and were exposed to an USWF using a 1 MHz CW sinusoidal signal for 15 min with an incident pressure amplitude of 0.1 MPa. Following USWF exposure, floating gels were incubated for 20 hrs at 37° C. and 8% $CO_2$ at which time they were removed from the wells and weighed. Percent contraction (FIGS. 6A and 6C) was calculated as (1−(test gel weight/ no-cell gel weight))×100. Data are average values from four experiments performed in quadruplicate. *p<0.05 vs. sham by paired t-test. Cell distribution (FIGS. 6B and 6D) in USWF-exposed (right) and sham gels (left) was analyzed using phase-contrast microscopy to correlate changes in percent contraction with USWF-mediated changes in the spatial distribution of cells. Scale bar, 200 μm.
Figure 6B:
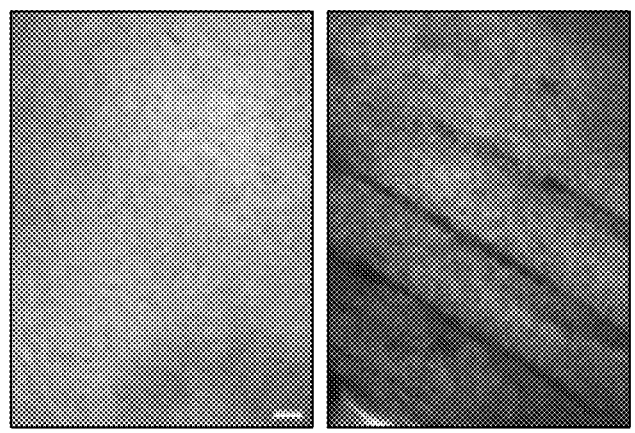
Figure 6C:
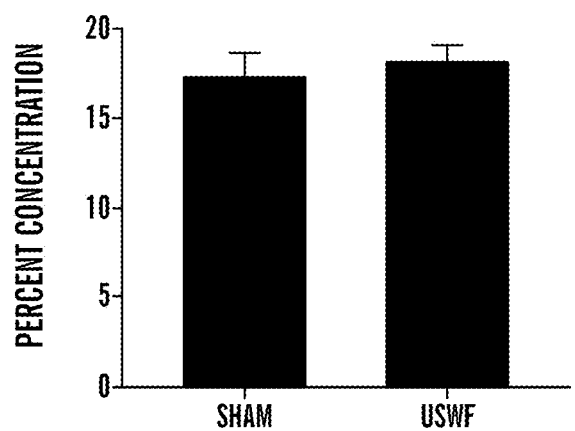
Figure 6D:
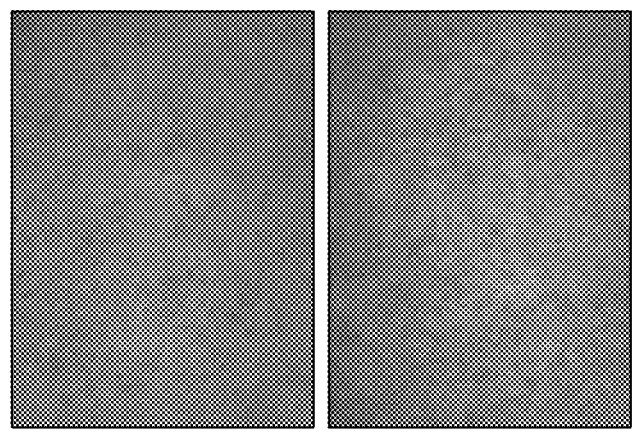

The biomechanical properties of normal human tissue and engineered tissue constructs are in part dictated by the organization of the extracellular matrix comprising that tissue or tissue construct (Vogel et al., "Local Force and Geometry Sensing Regulate Cell Functions," *Nat Rev Mol Cell Biol* 7:265-75 (2006), which is hereby incorporated by reference in its entirety). In turn, extracellular matrix organization is partly influenced by cell-derived forces. These forces are exerted on matrix components through intracellular tension generation due to cytoskeletal contractility (Hinz et al., "Mechanisms of Force Generation and Transmission by Myofibroblasts," *Curr Opin Biotechnol* 14:538-46 (2003); Hocking et al., "Stimulation of Integrin-mediated Cell Contractility by Fibronectin Polymerization," *J Biol Chem* 275:10673-82 (2000); and Lee et al., "Extracellular Matrix and Pulmonary Hypertension-control of Vascular Smooth Muscle Cell Contractility," *Am J Physiol Heart Circ Physiol* 274:H76-H82 (1998), which are hereby incorporated by reference in their entirety). Cell-mediated collagen gel contraction is a common measure of extracellular matrix remodeling by cells (Korff et al., "Tensional Forces in Fibrillar Extracellular Matrices Control Directional Capillary Sprouting," *J Cell Sci* 112:3249-58 (1999); Sieminski et al., "The Relative Magnitudes of Endothelial Force Generation and Matrix Stiffness Modulate Capillary Morphogenesis In Vitro," *Exp Cell Res* 297:574-84 (2004); and Vernon et al., "Contraction of Fibrillar Type I Collagen by Endothelial Cells: A Study In Vitro," *J Cell Biochem* 60:185-97 (1996), which are hereby incorporated by reference in their entirety). Changes in the extent of collagen gel contraction indicate alterations in ECM remodeling that can subsequently influence cell behavior (Sieminski et al., "The Relative Magnitudes of Endothelial Force Generation and Matrix Stiffness Modulate Capillary Morphogenesis In Vitro," *Experimental Cell Research* 297:574-584 (2004); Vernon et al., "Reorganization of Basement Membrane by Cellular Traction Promotes the Formation of Cellular Networks In Vitro," *Laboratory Investigation* 66:536-547 (1992); Korff et al., "Tensional Forces in Fibrillar Extracellular Matrices Control Directional Capillary Sprouting," *Journal of Cell Science* 112:3249-3258 (1999); Vernon et al., "Contraction of Fibrillar Type I Collagen by Endothelial Cells: A Study In Vitro," *Journal of Cellular Biochemistry* 60:185-197 (1996), which are hereby incorporated by reference in their entirety). To assess if a change in the spatial distribution of cells affects cell-mediated matrix remodeling, a collagen gel contraction assay was used to compare the extent of collagen gel contraction between USWF cell-organized and sham gels. A 2-fold increase in the contraction of collagen gels with USWF-induced cell organization was found as compared to sham gels with a random cell distribution (FIGS. 6A and 6B). Additional experiments were designed to demonstrate that this increase in collagen gel contraction was a result of the altered cell distribution and not an effect of the USWF exposure parameters on FN-/-MF tension generation. According to theory, increasing the viscosity of the suspending medium will inhibit USWF-induced movement of cells to the pressure nodes (Coakley et al., "Cell Manipulation in Ultrasonic Standing Wave Fields," *Journal of Chemical Technology and Biotechnology* 44:43-62 (1989), which is hereby incorporated by reference in its entirety). Based on this prediction, collagen gels with a homogeneous distribution of FN-/- MF were polymerized prior to USWF exposure. No differences in collagen gel contraction between USWF-exposed and sham samples were found and microscopic analysis confirmed the lack of localization of cells to the nodal planes (FIGS. 6C and 6D). These data indicate that cell-mediated ECM remodeling is altered in USWF cell-organized collagen gels.

Example 6

The Formation of Cell Bands Depends on USWF Pressure Amplitude

Figure 7:
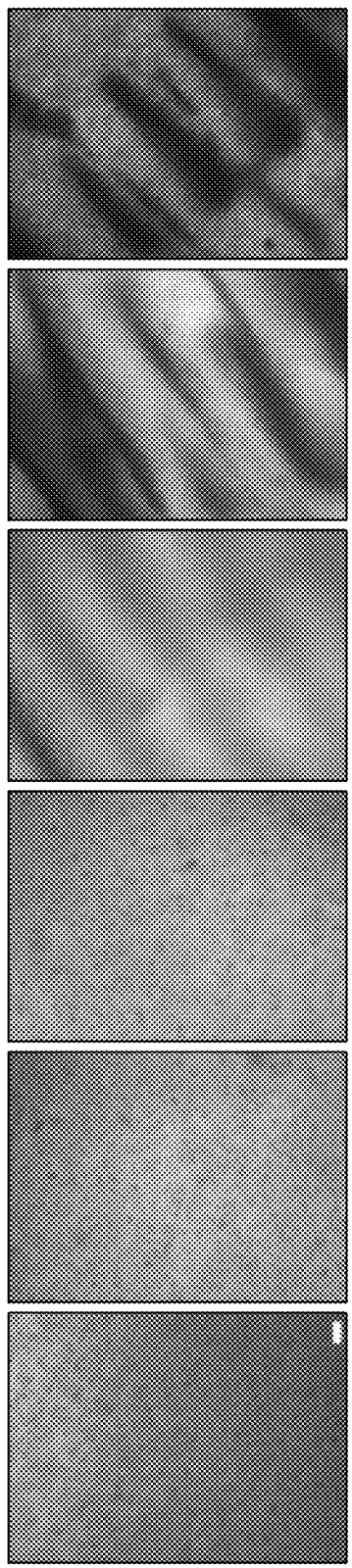
FIG. 7 is a series of photomicrographs illustrating cell banding as a function of USWF pressure amplitude. Fibronectin-null cells ($4\times10^6$ cell/ml) were suspended in collagen I solutions and were exposed at room temperature for 15 min to a continuous wave USWF (1 MHz source) with various peak pressure amplitudes. Representative phase-contrast images, from one of four experiments, indicate cell banding in samples exposed to 0.1 MPa and above. Scale bar, 200 μm.

The magnitude of the acoustic radiation force ($F_{rad}$) in an USWF has a second order dependence on pressure amplitude ($P_o$) and, as such, changing $P_o$ will affect the movement of cells to the pressure nodes (Eq. 1). Theoretical analysis of the forces acting on particles in an USWF predicts a threshold pressure for banding below which particles will not accumulate on the nodal planes (Coakley et al., "Cell Manipulation in Ultrasonic Standing Wave Fields," *J Chem Tech Biotechnol* 44:43-62 (1989), which is hereby incorporated by reference in its entirety). To determine the threshold pressure amplitude necessary to achieve cell banding within collagen gels, fibronectin-null cells suspended in type-I collagen solutions were exposed during the polymerization process to an USWF of various peak pressure amplitudes. Cell distribution was then analyzed using phase-contrast microscopy. As shown in FIG. 7, homogeneous cell distributions were observed within sham-exposed gels, as well as gels fabricated using an USWF with peak pressure amplitudes of 0.02 and 0.05 MPa. Exposing samples to an USWF with peak pressure amplitude of 0.1 MPa resulted in the formation of cell bands, indicating that the threshold pressure for USWF-induced cell banding in this system is ~0.1 MPa ($F_{rad}$=0.55 pN). When an USWF with pressure amplitude of 0.2 MPa is used to fabricate the collagen gels, cell bands appeared more dense. With a pressure amplitude of 0.3 MPa, the resulting cell bands were thicker and more localized to the center of the gel, likely due to the influence of secondary lateral acoustic radiation forces acting within the pressure nodal planes (Spengler et al., "Microstreaming Effects on Particle Concentration in an Ultrasonic Standing Wave," *AIChE J* 49:2773-82 (2003), which is hereby incorporated by reference in its entirety). These findings indicate that different USWF pressure amplitudes lead to variations in the patterns of banded cells within collagen gels.

Example 7

USWF Pressure Amplitude Has a Biphasic Effect on Cell-Mediated Collagen Gel Contraction The data indicate that USWF-induced cell organization enhances cell-mediated collagen gel contraction, and that the extent of cell banding is affected by the USWF pressure amplitude. To determine if different cell banded patterns affect the extent of collagen gel contraction, radial collagen gel contraction assays were used to compare levels of collagen gel contraction among gels fabricated at the six different USWF pressure amplitudes shown in FIG. 7. No differences in collagen gel contraction were observed among sham-exposed samples and samples exposed to either 0.02 or 0.05 MPa (FIG. 8A) where cells remain in a homogeneous distribution (FIG. 7). In contrast, a significant 1.5-fold increase in gel contraction occurred at 0.1 MPa (FIG. 8A), the pressure threshold for cell banding, where cells first become aligned into planar bands (FIG. 7). These results, obtained using gel diameter measurements, are similar to those reported in FIG. 6 using volumetric contraction assays, and therefore, provide additional evidence that USWF-induced cell banding enhances cell-mediated collagen gel contraction and matrix reorganization.

Figure 8B:
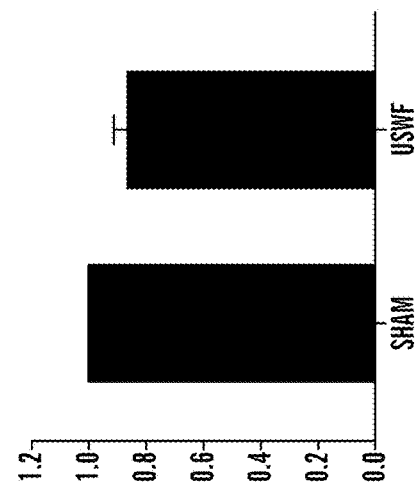
FIGS. 8A-8B are graphs showing the biphasic effect of USWF pressure amplitude on cell-mediated collagen gel contraction.
Figure 8A:
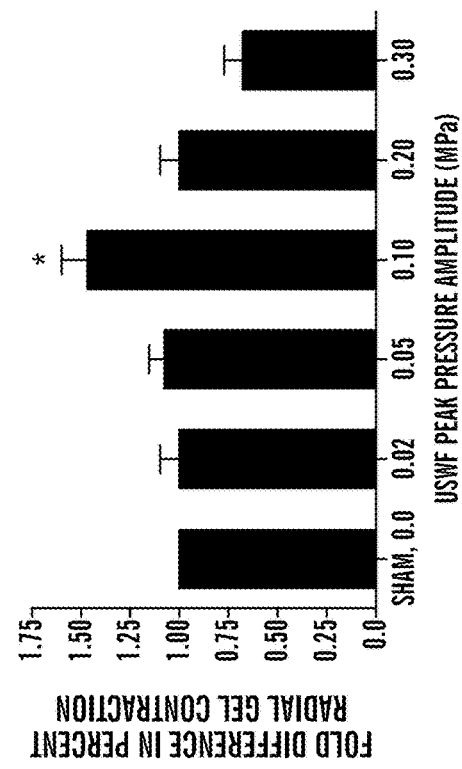

As the USWF pressure amplitude was increased above 0.1 MPa, collagen gel contraction levels decreased (FIG. 8A). At 0.3 MPa, a 30% decrease in contraction as compared to sham levels was observed (FIG. 8A). There were no significant differences in the number of viable cells between sham-exposed and 0.3 MPa USWF-exposed samples (FIG. 8B). Therefore, the decrease in collagen gel contraction was not due to cell death, but was more likely due to effects of the cell banded pattern that occurred at 0.3 MPa. These findings indicate that the effect of USWF pressure amplitude on cell-mediated collagen gel contraction is biphasic. This biphasic effect on collagen gel contraction can be attributed to the decrease in cell-extracellular matrix contacts formed as cell bands become more compact above the threshold pressure.

Figure 9:
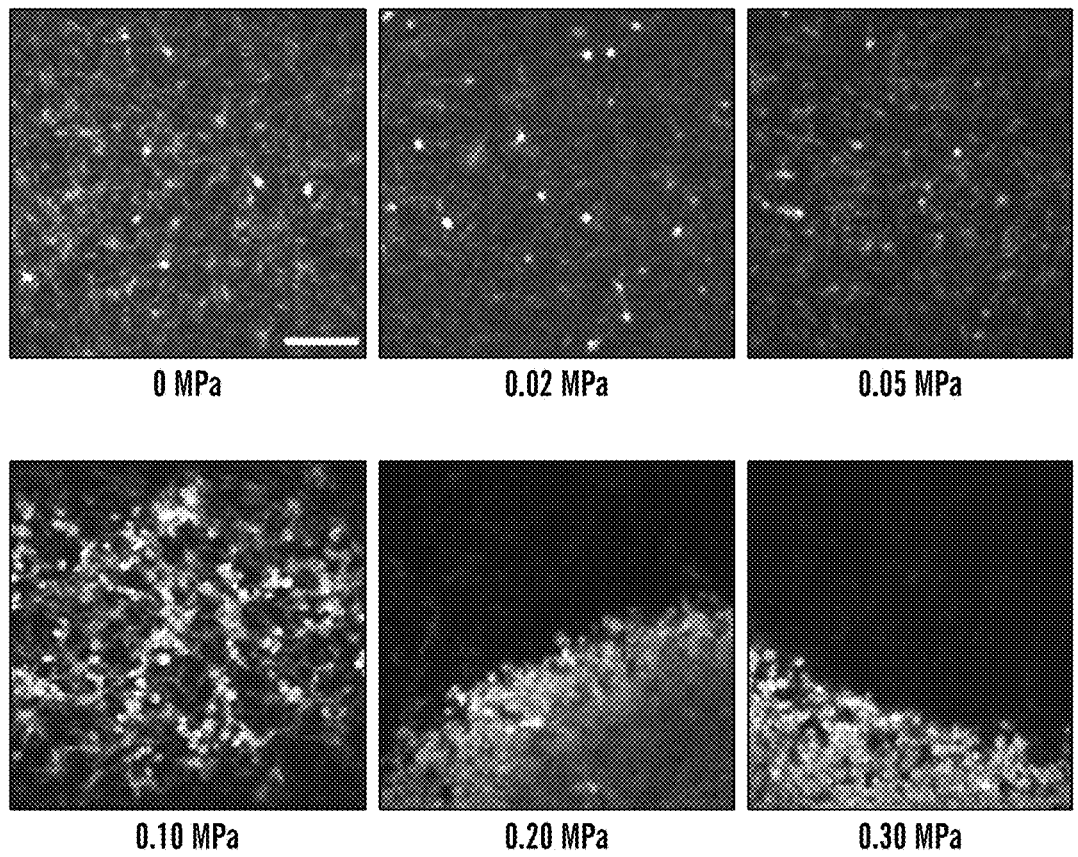
FIG. 9 is a series of fluorescent photomicrographs showing the biphasic effect of USWF pressure amplitude on cell-mediated collagen reorganization. Fibronectin-null cells ($4\times10^6$ cell/ml) suspended in collagen I solutions were exposed at room temperature for 15 min to a continuous wave USWF (1 MHz source) with various peak pressure amplitudes (0-0.30 MPa). Following 1 hr incubation at 37° C. and 8% $CO_2$, gels were fixed with 4% paraformaldehyde and imaged using second-harmonic generation microscopy as described infra. Representative merged images, from one of three experiments, are shown. Scale bar, 100 μm.

To directly assess collagen matrix organization relative to the cell banded areas formed using USWF of various pressure amplitudes, second-harmonic generation microscopy imaging of collagen fibers was performed. As shown in FIG. 9, short collagen fibrils were randomly organized in sham-exposed (0 MPa) cell-embedded collagen gels and in cell-embedded collagen gels exposed to either 0.02 or 0.05 MPa where cells remain in a homogeneous distribution. Exposure to 0.1 MPa resulted in areas of the gels where cells were loosely clustered and collagen fibrils were more elongated. These data clearly show that cells aligned into planar bands at the pressure threshold for cell banding have reorganized their surrounding collagen matrix, and thus, provide further evidence that USWF-induced cell banding enhances cell-mediated collagen matrix remodeling.

Extensive areas of cell bands were clearly visible in collagen gels exposed to 0.2 or 0.3 MPa, and short collagen fibers surrounding these areas were randomly oriented. These results indicate that as the USWF pressure amplitude increases beyond the pressure threshold for cell banding and cell bands become more dense, cell-mediated collagen matrix reorganization decreases. Therefore, the effect of USWF pressure amplitude on cell-mediated collagen matrix reorganization is biphasic and as such, these data both parallel and support the data showing that USWF pressure amplitude has a biphasic effect on collagen gel contraction. Taken together, these data indicate that radiation forces associated with an USWF can indirectly influence the relative location of extracellular proteins and thus, can be used to control extracellular-matrix dependent functions essential to tissue formation.

Discussion of Examples 1-7

Examples 1-7 above describe the development and use of ultrasound standing wave fields as a novel, non-invasive technology for organizing cells and cell-bound proteins within tissue engineered biomaterials. These studies have demonstrated that acoustic radiation forces associated with an USWF can be used to organize both mammalian cells and cell-associated proteins into discrete bands within collagen hydrogels. The density of the USWF-aligned cell bands was dependent on both cell number and pressure amplitude. Exposure of cells to USWF parameters utilized in the current study did not decrease cell viability. Furthermore, the USWF-aligned cell bands were stable for at least 20 hr.

Under appropriate conditions, the organization of cells into bands led to an increase in cell-mediated collagen gel contraction, as measured by both volumetric and radial changes, demonstrating an increase in cell function in response to cell alignment. The increase in collagen gel contraction in response to USWF exposure did not occur if the collagen/cell samples were allowed to polymerize prior to USWF exposure, strongly suggesting that the increases in cell contractility and collagen fibril reorganization were mediated by the organization of cells into bands and were not an indirect effect of ultrasound exposure on individual cells. The extent of collagen contraction was dependent upon the spatial distribution of cells in the gel. No increase in collagen gel contraction was observed in response to USWF exposure at pressure amplitudes that did not produce cell banding. At the other extreme, no increase in collagen gel contraction was observed in response to USWF at pressure amplitudes that produced densely packed cell bands. However, exposure of samples to an USWF that leads to the clustering of cells into planar bands within the gel resulted in a significant increase in collagen contraction above sham gels with a homogenous cell distribution.

Clustering of cells into planar bands in response to an USWF also led to changes in collagen fibril organization and length. Second-harmonic generation microscopic images showed that short collagen fibers were randomly organized in gels exposed to USWF at pressure amplitudes that did not produce cell banding as well as pressure amplitudes that produced densely packed cell bands. In contrast, elongated collagen fibers were observed within loosely clustered cell banded areas indicating enhanced cell-mediated collagen matrix remodeling in these samples. These results are consistent with the biphasic results of the collagen gel contraction investigations. Hence, an important downstream effect of USWF-mediated cell alignment is enhanced extracellular matrix remodeling. Thus, the use of USWF to specifically control cell and extracellular organization is a promising new approach for engineering complex tissues in vitro.

Acoustic radiation forces exerted on extracellular matrix proteins were too small to directly organize proteins in the system used in this study. However, the use of an USWF can indirectly effect the organization of proteins in the extracellular matrix by two avenues. First, as explained in the paragraph above, increased collagen fibril length and organization was observed in gels exposed to an USWF at pressure amplitudes that increased collagen gel contraction. Thus, a downstream effect of USWF-induced cell banding is the resultant cellular remodeling of the surrounding extracellular matrix. Second, the extracellular matrix protein, fibronectin, could be aligned into bands within the collagen gel using an USWF if the fibronectin molecules were first bound to the cell surface. Thus, USWF technology can be used spatially organize cells within engineered tissues and to co-locate active or inactive cell-bound molecules.

The use of an USWF has numerous advantages as a noninvasive technology to spatially organize cells and cell-bound molecules in engineered tissues, and thereby influence cell function. The acoustic radiation force acts directly on the cells and thus the approach does not require any prior modification of the cell surface. Various hydrogels that undergo phase transitions could be adapted to this technique. Changing frequency of the ultrasound field will affect spacing of cell bands, and multiple transducers could be used to produce more complex patterns of cells within engineered biomaterials.

Example 8

Endothelial Cell Sprouting is Observed from USWF-Induced EC Bands

Figure 10A:
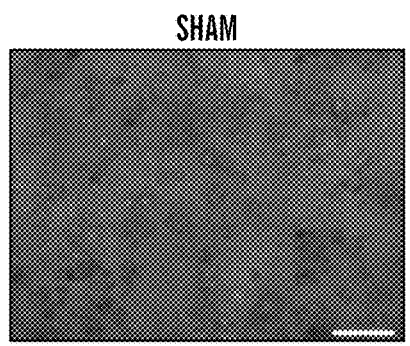
FIGS. 10A-10B shows endothelial cell sprouts emerging from USWF-induced endothelial cell bands. Human umbilical vein endothelial cells (HUVEC; $1\times10^6$ c/ml) suspended in a collagen I solution were exposed to an USWF using a 1 MHz CW sinusoidal signal for 15 min with an incident pressure amplitude of 0.1 MPa. Following USWF exposure, gels were incubated for 24 hrs at 37° C. and 5% CO2 and then imaged using phase-contrast microscopy. Endothelial cell sprouts (arrows) can only be seen in USWF-exposed gels (FIG. 10B) and not in sham gels (FIG. 10A). Images represent similar results obtained from six experiments performed in triplicate. Scale bar, 100 μm.
Figure 10B:
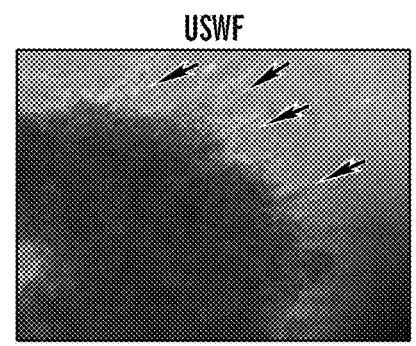

Multicellular spheroids of endothelial cells are commonly used to study sprouting angiogenesis in 3D assays (Vailhe et al., "In Vitro Models of Vasculogenesis and Angiogenesis," *Laboratory Investigation* 81(4):439-452 (2001), which is hereby incorporated by reference in its entirety). To investigate if the organization of EC into a banded pattern within collagen gels supports endothelial cell sprouting, human umbilical vein endothelial cells (HUVEC) were subjected to an USWF and resulting endothelial cell bands were analyzed for the formation of endothelial cell sprouts. As shown in FIG. 10B, endothelial cells sprouting from a cell band can be seen 24 hrs after USWF exposure. Sprouting was absent in sham gels where a rounded cell morphology was found. These preliminary observations suggest that ultrasonic radiation force-induced endothelial cell organization promotes an angiogenic phenotype in endothelial cell.

Example 9

The Use of Ultrasound to Promote Angiogenesis within 3D Collagen Constructs

Ultrasound-mediated changes in endothelial cell and ECM protein organization is expected to induce neovessel formation for the vascularization of 3D tissue constructs. The development of vascular systems within engineered tissues is essential to the advancement of the tissue engineering field (M.A.T.E.S.I.W.G.

Advancing Tissue Science and Engineering: A Foundation for the Future—A Multi-Agency Strategic Plan. 2007; Griffith et al., "Tissue Engineering-Current Challenges and Expanding Opportunities," *Science* 295:1009-1014 (2002); and Nerem R. M., "Tissue Engineering: The Hope, the Hype, and the Future," *Tissue Engineering* 12:1143-1150 (2006), which are hereby incorporated by reference in their entirety).

New vascular networks can be induced to grow within 3D constructs by stimulating angiogenic endothelial cell behaviors (Nomi et al., "Principals of Neovascularization for Tissue Engineering," *Molecular Aspects of Medicine* 23:463-483 (2002); Laschke et al., "Angiogenesis in Tissue Engineering: Breathing Life into Constructed Tissue Substitutes," *Tissue Engineering* 12(8):2093-2104 (2006); Soker et al., "Systems for Therapeutic Angiogenesis," *World Journal of Urology* 18:10-18 (2000); and Lokmic et al., "Engineering the Microcirculation," *Tissue Engineering* 14(1):87-103 (2008), which are hereby incorporated by reference in their entirety) through the aggregation of endothelial cells into multicellular structures (Korff et al., "Integration of Endothelial Cells in Multicellular Spheroids Prevents Apoptosis and Induces Differentiation," *The Journal of Cell Biology* 143(5):1341-1352 (1998) and Ino et al., "Application of Magnetic Force-Based Cell Patterning for Controlling Cell-Cell Interactions in Angiogenesis," *Biotechnology and Bioengineering* 102(3):882-890 (2009), which are hereby incorporated by reference in their entirety), controlling the organization of the surrounding ECM (Francis et al., "Endothelial Cell-Matrix Interactions in Neovascularization," *Tissue Engineering* 14(1):19-32 (2008) and Sottile J., "Regulation of Angiogenesis by Extracellular Matrix," *Biochimica et Biophysica Acta* 1654:13-22 (2004), which are hereby incorporated by reference in their entirety), and exposing endothelial cells to mechanical forces (Iba et al., "Effect of Cyclic Stretch on Endothelial Cells from Different Vascular Beds," *Circulatory Shock* 35:193-198 (1991); Ando et al., "The Effect of Fluid Shear Stress on the Migration and Proliferation of Cultured Endothelial Cells," *Microvascular Research* 33:62-70 (1987); Vouyouka et al., "Ambient Pulsatile Pressure Modulates Endothelial Cell Proliferation," *Journal of Molecular and Cellular Cardiology* 30(3):609-615 (1998); which are hereby incorporated by reference in their entirety). The data described supra indicates that USWF radiation forces aggregate cells into multicellular arrangements, organizes fibronectin into a banded pattern, enhances cell-mediated collagen remodeling, and promotes endothelial cell sprouting. These results, together with previous findings that ultrasound can enhance angiogenesis (Barzelai et al., "Low-Intensity Ultrasound Induces Angiogenesis in Rat Hind-Limb Ischemia,"*Ultrasound in Medicine and Biology* 32(1):39-145 (2006); Young et al., "The Effect of Therapeutic Ultrasound on Angiogenesis," *Ultrasound in Medicine and Biology* 16:261-269 (1990); Raz et al., "Cellular Alterations in Cultured Endothelial Cells Exposed to Therapeutic Ultrasound Irradiation," *Endothelium* 12:201-213 (2005); Mizrahi et al., "Ultrasound-Induced Angiogenic Response in Endothelial Cells," *Ultrasound in Medicine and Biology* 33(11):1818-1829 (2007), which are hereby incorporated by reference in their entirety), suggest that ultrasound can play a role in promoting an angiogenic response in endothelial cells for the formation of neovascular networks in 3D tissue constructs.

Figure 11A:
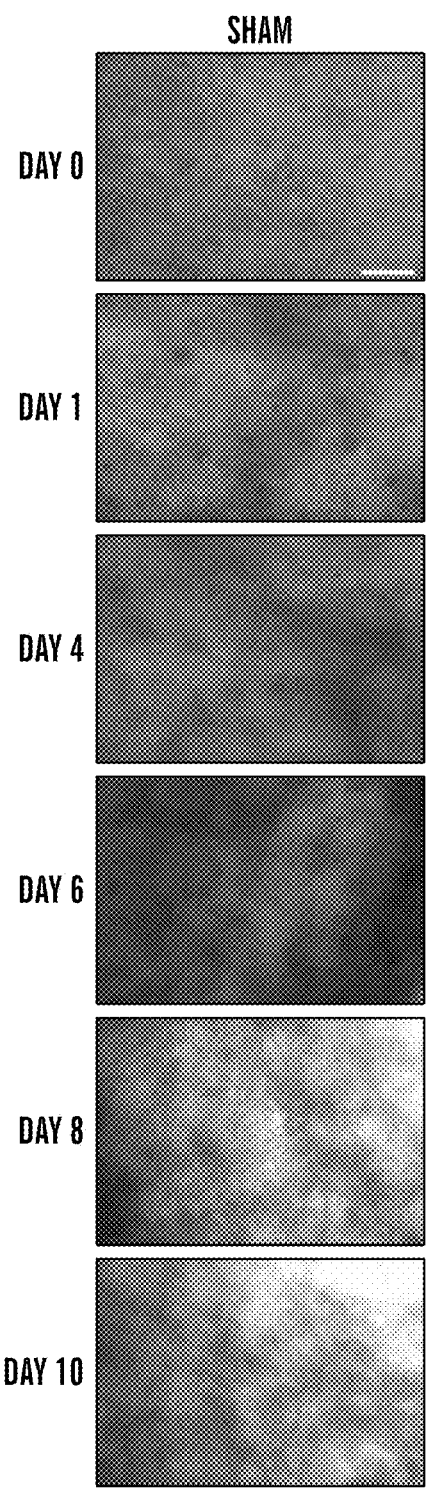
FIGS. 11A-11B are a series of photomicrographs tracking the capillary-like endothelial cell sprouts emerging from USWF-induced endothelial cell bands. HUVEC were suspended at $1\times10^6$ cell/ml in a neutralized type-I collagen solution and were exposed to a 1 MHz USWF with a peak pressure amplitude of 0.2 MPa for a 15 min duration at room temperature to promote the formation of multicellular endothelial cell bands (FIG. 11B). Sham samples were treated in the exact same manner as USWF-exposed samples but did not receive USWF treatment (FIG. 11A). Representative phase-contrast images collected at the indicated time points following USWF exposure are shown. Multiple capillary-like sprouts can be seen emerging from the endothelial cell banded area. Arrow, same sprout over time. Scale bar, 100 μm.
Figure 11B:
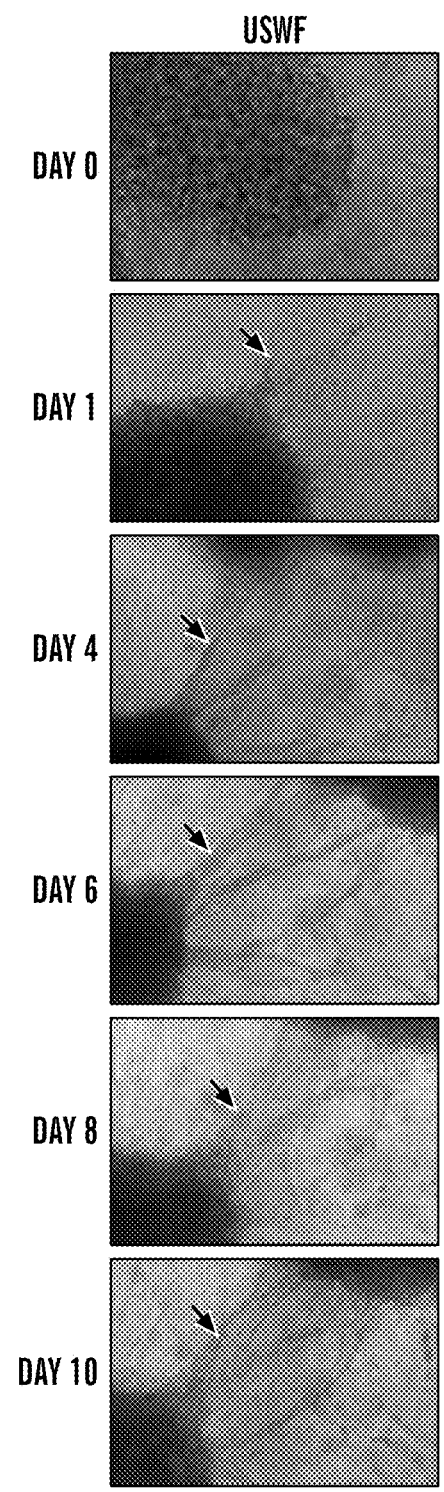

The formation of neovessels in response to USWF-induced endothelial cell organization was assessed at various times over a 10-day period using phase-contrast microscopy. Human umbilical vein endothelial cells were suspended at $1 \times 10^6$ cell/ml in a neutralized type-I collagen solution and exposed to a 1 MHz USWF with a peak pressure amplitude of 0.2 MPa for a 15 min duration at room temperature to promote the formation of multicellular endothelial cell bands. Cell-embedded collagen gels were incubated at 37° C. and 5% $CO_2$ for an additional 10 days. Sham samples were treated in the exact same manner as USWF-exposed samples but did not receive USWF treatment. Representative phase-contrast images of sham and USWF-treated samples were collected on Day 1, 4, 6, 8, and 10 (FIGS. 11A-11B; scale bar, 100 µm). Multiple capillary-like sprouts emerged from areas of organized endothelial cell bands by Day 1 in USWF-exposed samples (FIG. 11B, "USWF"). In contrast, endothelial cells were randomly distributed in sham samples (FIG. 11A, "Sham"). The capillary-like sprouts that formed in USWF-exposed samples increased in length and width over the ten-day period (FIG. 11B). In addition, numerous branches were observed.

Figure 12A:
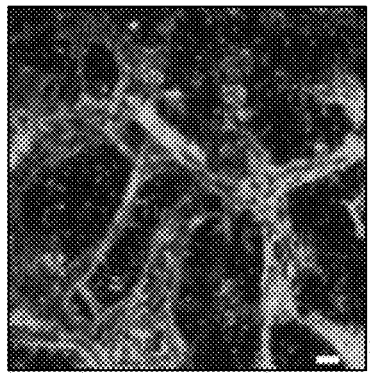
FIGS. 12A-12B are fluorescent photomicrographs showing that USWF-induced endothelial cell sprouts are multicellular structures. Four days following Sham (FIG. 12A) or USWF (FIG. 12B) exposure, samples were fixed in 4% paraformaldehyde and permeabilized with 0.5% TritonX-100. Cell nuclei were visualized by staining with DAPI and HUVEC were visualized by staining with anti-human CD31 monoclonal antibody followed by AlexaFluor-594 conjugated anti-mouse IgG. Two-photon microscopy was used to collect images along the z-axis in 1 μm slices. Images were then projected onto the z-plane using ImageJ software. Scale bar, 15 μm.
Figure 12B:
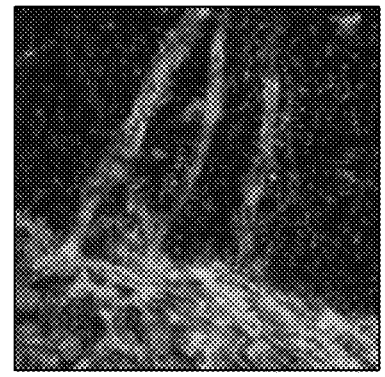

To assess cell morphology within the USWF-induced capillary-like structures, USWF- and sham-exposed samples were fixed four days after USWF exposure, and then processed for immunofluorescence microscopy. Cell nuclei were visualized by staining with DAPI (FIGS. 12A-12B) and human umbilical vein endothelial cells were visualized by staining with anti-human CD31 monoclonal antibody followed by AlexaFluor-594 conjugated anti-mouse IgG (FIGS. 12A-12B). Two-photon microscopy was used to collect images along the z-axis in 1 µm slices. Images were then projected onto the z-plane using ImageJ software. Endothelial cells in sham-exposed samples demonstrated random network formation and condensed nuclei, indicative of cell death (FIG. 12A). In contrast, capillary sprouts in USWF-exposed samples were well-organized, multicellular structures that clearly extended from endothelial cell bands (FIG. 12B, "USWF"; scale bar, 15 microns).

Figure 13A:
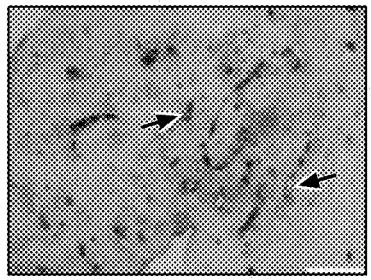
FIGS. 13A-13B are photomicrographs demonstrating that USWF-induced endothelial cell sprouts contain endothelial cell-lined lumen. Four days following USWF exposure (FIG. 13B), samples were fixed in 4% paraformaldehyde and processed normally for histology. Sham samples were treated in the exact same manner as USWF-exposed samples but did not receive USWF treatment (FIG. 13A). Four-micrometer thick gel cross-sections were stained with H&E to differentiate cells from the surrounding collagen matrix. HUVEC-lined lumens in representative images are indicated by the arrows. Scale bar, 100 μm.
Figure 13B:
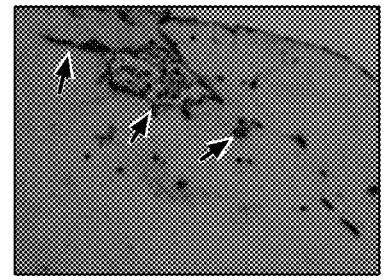

To determine whether lumens were formed within the USWF-induced capillary-like structures, USWF- and sham-exposed samples were fixed and processed for histological analysis four days after USWF exposure. Four-micrometer thick gel cross-sections were stained with hematoxylin and eosin to differentiate cells from the surrounding collagen matrix. Large, cell-lined lumens with smaller branching lumen containing sprouts were observed USWF-exposed (FIG. 13B) samples compared to sham-exposed gels (FIG. 13A) (scale bar, 100 µm).

Figure 14A:
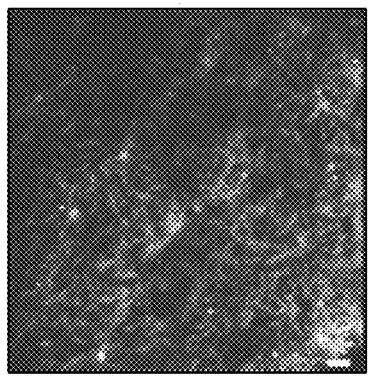
FIGS. 14A-14B are fluorescent photomicrographs showing reorganization of collagen fibers surrounding USWF-induced capillary sprouts in the direction of sprout outgrowth. One day following USWF exposure, samples were fixed in 4% paraformaldehyde (FIG. 14B). Sham samples were treated in the exact same manner as USWF-exposed samples but did not receive USWF treatment (FIG. 14A). Collagen type-I fibers were visualized using second harmonic generation microscopy imaging on a two-photon microscope. HUVEC were visualized using their intrinsic auto-fluorescence. Scale bar, 1 μm.
Figure 14B:
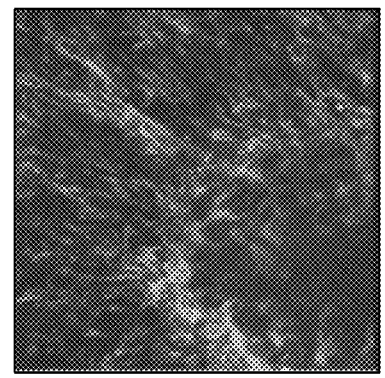

To assess extracellular matrix remodeling in USWF- and sham-exposed gels, collagen type-I fibers were visualized using second harmonic generation microscopy imaging on a two-photon microscope (FIGS. 14A-14B; scale bar, 15 microns). Human umbilical vein endothelial cells were visualized simultaneously using intrinsic auto-fluorescence (FIGS. 14A-14B). Collagen fibers were organized in linear, parallel arrays extending outwards from the endothelial cell bands in USWF-exposed (FIG. 14B), but not sham-exposed (FIG. 14A) samples.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An in vitro vascularized engineered tissue construct, wherein said construct has a thickness in three-dimensions of at least 2 mm, said construct comprising:
   a polymerized biological support material comprising one or more recombinant fibronectin peptide mimetics;
   endothelial cells organized into two or more three-dimensional sheets or columns within different planes of said polymerized biological support material; and
   lumen containing neovessels defined by said endothelial cells, said lumen containing neovessels extending within and/or between said three-dimensional sheets or columns of endothelial cells.

2. The vascularized engineered tissue construct of claim 1, wherein the biological support material is selected from the group consisting of collagen gel, fibrin gel, hydrogel, growth factor reduced Matrigel, and Matrigel.

3. The vascularized engineered tissue construct of claim 1, wherein said construct further comprises a three-dimensional biological support material selected from the group consisting of filaments, meshes, foams, gels, ceramics, a porous polymeric scaffold, a synthetic polymeric scaffold, and acellularized extracellular matrix material.

4. The vascularized engineered tissue construct of claim 1, wherein lumen-containing neovessels originate from one of the three-dimensional sheets or columns of endothelial cells and interconnect with lumen-containing neovessels that originate from a different three-dimensional sheet or column of endothelial cells.

5. The vascularized engineered tissue construct of claim 1, wherein said lumen-containing neovessels have internal diameters of 0.5 mm or less.

6. The vascularized engineered tissue construct of claim 1, wherein said construct further comprises one or more additional cell type.

7. The vascularized engineered tissue construct of claim 6, wherein the one or more additional cell type is selected from the group consisting of smooth muscle cells, cardiac muscle cells, cardiac myocytes, platelets, epithelial cells, urothelial cells, fibroblasts, embryonic fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, adipocytes, embryonic stem cells, mesenchymal stem cells, neural cells, endothelial progenitor cells, hematopoietic cells, and precursor cells.

8. The vascularized engineered tissue construct of claim 7, wherein the one or more additional cell type is neural cells.

9. The vascularized engineered tissue construct of claim 1, wherein said construct comprises a vascularized muscular construct, a vascularized esophageal construct, a vascularized intestinal construct, a vascularized rectal construct, a vascularized ureteral construct, a vascularized cartilaginous construct, a vascularized cardiac construct, a vascularized liver construct, a vascularized bladder construct, a vascularized kidney construct, a vascularized pancreatic construct, a vascularized skeletal construct, a vascularized filamentous/ligament construct, a vascularized lung construct, a vascularized neural construct, a vascularized bone construct, or a vascularized skin construct.

10. The vascularized engineered tissue construct of claim 9, wherein said construct comprises a vascularized neural construct.

11. A method of treating a subject in need of a tissue repair or tissue replacement, said method comprising:
   selecting a subject in need of tissue repair or tissue replacement;
   providing the vascularized engineered tissue construct of claim 1; and
   implanting the vascularized engineered tissue construct into a region of the selected subject in need of tissue repair or tissue replacement.

12. The method of claim 11, wherein the subject is in need of neural tissue repair or replacement.

13. The method of claim 11, wherein the vascularized engineered tissue construct is a vascularized engineered neural tissue construct.

14. The method of claim 11, wherein the vascularized engineered tissue construct comprises endothelial cells obtained from the selected subject.

15. The method of claim 11, wherein the subject is a human subject.

\* \* \* \* \*